United States Patent
Ma et al.

(10) Patent No.: US 11,369,575 B2
(45) Date of Patent: Jun. 28, 2022

(54) PPARα AGONIST COMPOSITIONS AND METHODS OF USE

(71) Applicant: The Board of Regents of the University of Oklahoma, Norman, OK (US)

(72) Inventors: Jian-xing Ma, Edmond, OK (US); Fangfang Qiu, Oklahoma City, OK (US); Qingguo Xu, Glen Allen, VA (US); Tuo Meng, Richmond, VA (US)

(73) Assignees: The Board of Regents of the University of Oklahoma, Norman, OK (US); Virginia Commonwealth University, Intellectual Property Foundation, Richmond, VA (US)

( * ) Notice: Subject to any disclaimer, the term of this patent is extended or adjusted under 35 U.S.C. 154(b) by 0 days.

(21) Appl. No.: 16/822,964

(22) Filed: Mar. 18, 2020

(65) Prior Publication Data
US 2020/0297651 A1    Sep. 24, 2020

Related U.S. Application Data

(60) Provisional application No. 62/821,267, filed on Mar. 20, 2019.

(51) Int. Cl.
*A61K 9/51* (2006.01)
*A61K 31/216* (2006.01)

(52) U.S. Cl.
CPC .......... *A61K 9/5138* (2013.01); *A61K 9/5161* (2013.01); *A61K 31/216* (2013.01)

(58) Field of Classification Search
None
See application file for complete search history.

(56) References Cited

U.S. PATENT DOCUMENTS 6,190,591 B1 *  2/2001  van Lengerich .......... B29B 7/72
                                                 264/141

OTHER PUBLICATIONS

Wright et al. (Medical management of diabetic retinopathy: Fenofibrate and ACCORD eye studies, Eye (2011) 25, 843-849). (Year: 2011).*

* cited by examiner

*Primary Examiner* — Melissa S Mercier
(74) *Attorney, Agent, or Firm* — Hall Estill Law Firm

(57) ABSTRACT

Pharmaceutical particles having an inner portion comprising an agonist of peroxisome proliferator-activated receptor α (PPARα) and a biodegradable polymer; and an outer coating comprising an emulsifier which surrounds the inner portion, wherein the agonist may be a fibrate, and the particle contains at least about 5 wt % to about 25 wt % of the agonist, and wherein the particle has a sustained delayed release of the agonist in a range of at least about 1 to 12 months when in an aqueous solution or physiological environment. The pharmaceutical particles may be used, for example, to treat diseases and conditions such as ocular disorders which benefit from PPARα agonism.

12 Claims, 26 Drawing Sheets
(22 of 26 Drawing Sheet(s) Filed in Color)

Untreated

Blank-NP

Feno-NP

PPARα AGONIST COMPOSITIONS AND METHODS OF USE

CROSS REFERENCE TO RELATED APPLICATIONS/INCORPORATION BY REFERENCE STATEMENT

The present patent application claims priority under 37 CFR § 119(e) to United States Provisional Patent Application U.S. Ser. No. 62/821,267, filed on Mar. 20, 2019, the entire contents of which are hereby expressly incorporated herein by reference.

GOVERNMENT SUPPORT

This invention was made with government support under Grant Numbers EY019309 and EY027827 awarded by the National Institutes of Health (NIH). The government has certain rights in the invention.

BACKGROUND

Retinal neovascularization (RNV) and choroid neovascularization (CNV) are associated with a wide range of ocular diseases such as diabetic retinopathy (DR), neovascular age-related macular degeneration (AMD), retinopathy of prematurity (ROP), and central and branch retina vein occlusion. Among these diseases, DR is the leading cause of visual loss in the working age population, while neovascular AMD is the leading cause of visual impairment in the elderly people in industrialized countries. Vascular leakage (hyperpermeability) and neovascularization (NV) are the common features of these diseases and the major causes of visual impairment. Laser photocoagulation, photodynamic therapy, surgical interventions have been important treatment options for neovascular disease. However, these treatments are often associated with unwanted vision-damaging side effects. Because VEGF plays a key role in the pathological NV, anti-VEGF agents such as bevacizumab, ranibizumab, pegaptanib, and aflibercept have emerged as current drugs for treating RNV and CNV. However, the anti-VEGF drugs are not always effective for all patients. Approximately half of the patients do not show improved vision after the anti-VEGF therapy, and approximately 10% of patients do not respond at all to the treatment. Anti-VEGF drugs are also not effective for the neuronal cell death, another pathological change in AMD and DR. Moreover, VEGF functions as a retinal neurotrophic factor and its blockade under retinal stress conditions may accelerate retinal cell death. In addition, they are associated with high costs and systemic risks such as stroke and thromboembolic events. They are also associated with short duration of efficacy and require repetitive intravitreal (IVT) injections to maintain the therapeutic effects. The frequent visits and injections are difficult for DR and AMD patients, and the risks of retinal detachment and endophthalmitis will increase with the IVT injection frequency. Therefore, novel safe agents and drug delivery system that can achieve long-term effects on these diseases have received great attention.

Fenofibrate, a prodrug of fenofibric acid, is a widely prescribed drug to treat dyslipidemia in clinic. Fenofibrate, a peroxisome proliferator-activated receptor α (PPARα) agonist, has also displayed anti-angiogenic and anti-inflammatory activities. Fenofibrate may offer some advantages over anti-VEGF agents, such as low-cost, fewer side effects and neuroprotective effects. In clinical trials, it displayed beneficial effects on DR in type 2 diabetic patients, independent of its effect on dyslipidemia. Moreover, it has been demonstrated that systemic administration of fenofibrate has robust therapeutic effects on DR and neovascular AMD in animal models. However, fenofibrate has a short half-life with an elimination time of about 20 h in the blood after oral administration, requiring daily systemic dosing. The fenofibrate level in the retina, like other drugs, is low after oral administration because of the blood-retina barrier. No fenofibrate or fenofibric acid was detected in Brown Norway rats' eyes following oral administration of fenofibrate. In order to achieve therapeutic fenofibrate level in posterior ocular segment, high oral doses up to 200 mg/60 kg/day are required for patients, which can lead to high-dose induced side effects such as nephrotoxicity. Furthermore, we have demonstrated that the therapeutic effect of fenofibrate on DR is independent of its systemic effects, and the efficacy can be achieved through IVT injection. However, small molecular weight drugs, including fenofibrate, demonstrated fast clearance from the vitreous through two main routes: the anterior route via aqueous turnover and the posterior route via uveal blood flow. In previous work, inhibitory effects of fenofibrate on retinal vascular leakage in STZ-induced diabetic rats and in oxygen-induced retinopathy (OIR) rats were transient, lasting for about 4 days after a single IVT injection. AMD and DR are chronic and progressive, requiring long-term treatments. Thus, frequent intraocular injections of fenofibrate are needed for its translational application for these chronic diseases. Moreover, in preclinical studies, fenofibrate was to be formulated with organic solvents (e.g. DMSO), and the frequent IVT injections containing organic solvents are not practical and can cause retinal apoptosis and retinal dysfunction. Improved compositions for delivery of drugs to the eye would therefore be desirable. It is to addressing this need that the present disclosure is directed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
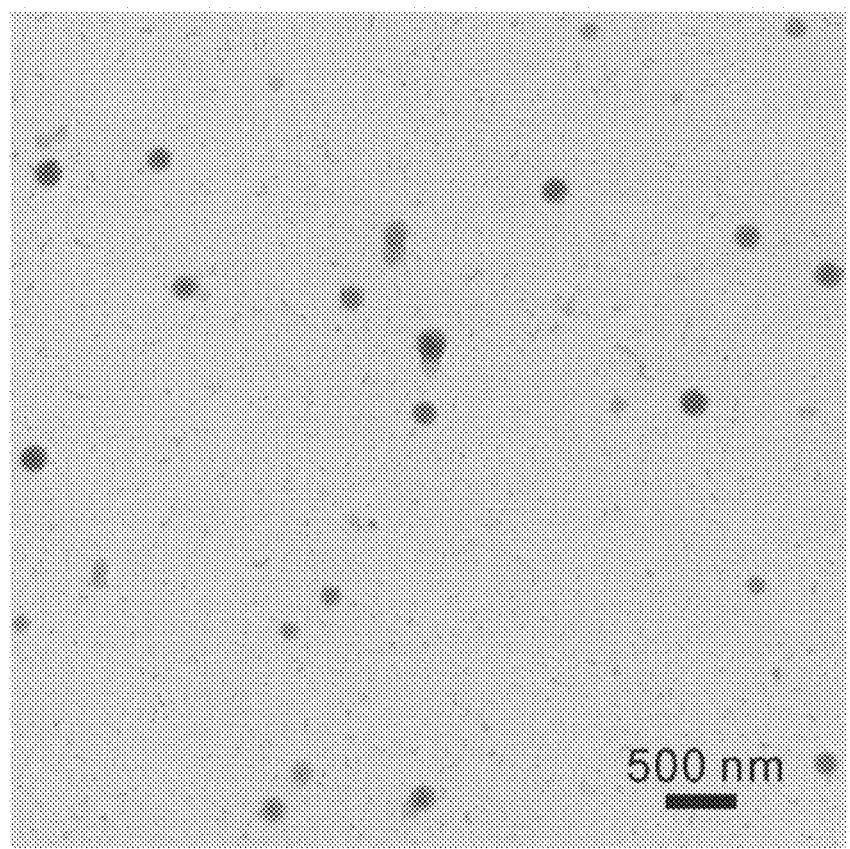
FIG. 1A shows a representative transmission electron microscope image of nanoparticles (NPs) made of fenofibrate (Feno-NPs) encapsulated by poly(lactic-co-glycolic acid) (PLGA) of 34 kDa (Feno-NP$_{PLGA34kDa}$).

In at least certain embodiments, the present disclosure is directed to biodegradable polymeric microparticle and nanoparticle (M/NP) formulations containing agonists of peroxisome proliferator-activated receptor α (PPARα) including, but not limited to, fenofibrate, pemafibrate, clofibrate, gemfibrozil, ciprofibrate, bezafibrate, ABT-335 (the choline salt of fenofibric acid), etofibrate, pirifibrate, beclofibrate, GW 9578, GW 7647, GW 590735, and GFT505, and combinations thereof. In one non-limiting embodiment, the biodegradable polymer is combined with and entraps the PPARα agonist to form an inner portion (inner core) of a nanoparticle or microparticle having an outer coating made from an emulsifier. The PPARα agonist-containing M/NPs formed in accordance with the present disclosure achieve high drug loading and prolonged drug release. The M/NPs may be made of any suitable polymer having a molecular weight (Mw), calculated according to weight average molecular weight and a molecular composition that function to provide high drug loading capacity and extended release of the PPARα agonist in accordance with the present disclosure.

In one non-limiting embodiment, the biodegradable polymer which is combined with and entraps the PPARα agonist to form the inner portion of the M/NP comprises poly(lactic-co-glycolic acid) (PLGA), and the emulsifier which forms the outer coating of the M/NP is poly (vinyl alcohol) (PVA). For example, the PLGA may have a weight average Mw in a range of 5 kDa to 100 kDa, and more particularly in a range of 25 kDa to 65 kDa. Other non-limiting examples of polymer formulations include PEG-PLGA(PLA) and PEG-PLGA/blend M/NPs, e.g., PLGA and PEG covalently conjugated to PLGA ($M_w$, 45 kDa) (PLGA45k-PEG5k). The duration of sustained extended release of the PPARα agonist from the M/NPs may be, for example, from at least about 1 month to at least about 6 months to at least about 9 months to at least about 12 months.

Before further describing various embodiments of the compounds, compositions and methods of the present disclosure in more detail by way of exemplary description, examples, and results, it is to be understood that the compounds, compositions, and methods of present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning; and the embodiments and examples are meant to be exemplary, not exhaustive. Also, it is to be understood that the phraseology and terminology employed herein is for the purpose of description and should not be regarded as limiting unless otherwise indicated as such. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure. All of the compounds, compositions, and methods of production and application and use thereof disclosed herein can be made and executed in light of the present disclosure. Thus, while the compounds, compositions, and methods of the present disclosure have been described in terms of particular embodiments, it will be apparent to those of skill in the art that variations may be applied to the compounds, compositions and/or methods and in the steps or in the sequence of steps of the methods described herein without departing from the concept, spirit, and scope of the inventive concepts described herein.

All patents, published patent applications, and non-patent publications mentioned in the specification or referenced in any portion of this application are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" and "approximately" are used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20%, or ±15%, or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 75% of the time, or at least 80% of the time, or at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment.

The term "pharmaceutically acceptable" refers to compounds, compositions, and particles which are suitable for administration to humans and/or animals without undue adverse side effects such as toxicity, irritation and/or allergic response commensurate with a reasonable benefit/risk ratio. The compounds of the present disclosure may be combined with one or more pharmaceutically-acceptable excipients, including carriers, vehicles, diluents, and adjuvents which may improve solubility, deliverability, dispersion, stability, and/or conformational integrity of the compounds or conjugates thereof. The term "pharmaceutical particle" refers to a pharmaceutically acceptable nanoparticle and/or microparticle containing an active agent as defined herein.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The term "nanoparticle," as used herein, generally refers to a particle having a diameter, such as an average diameter, from about 1 nm, to about 5 nm, to about 10 nm, to about 50 nm up to about 1000 nm, including, for example, particles having an average diameter of 5 nm, to 10 nm, up to about 100 nm, up to about 200 nm, up to about 300 nm, up to about 400 nm, up to about 500 nm, up to about 600 nm, up to about 700 nm, up to about 800 nm, or up to about 900 nm or more. The particles can have any shape. Nanoparticles having a spherical shape are generally referred to as "nanospheres".

The term "microparticle," as used herein, generally refers to a particle having a diameter, such as an average diameter, from about 1 micron (micrometer) to about 100 microns, for example including particles having an average diameter from about 1 micron to about 50 microns, from about 1 micron to about 40 microns, from about 1 micron to about 30 microns, from about 1 micron to about 25 microns, from about 1 micron to about 20 microns, from about 1 micron to about 10 microns, or from about 1 to about 5 microns. The microparticles can have any shape. Microparticles having a spherical shape are generally referred to as "microspheres".

The term M/NP (M/NPs—plural) is intended to refer to a particle of the present disclosure which may be either a microparticle or a nanoparticle, depending on the particular composition and method of particle formulation. The term M/NPs may refer to a composition comprising both nanoparticles and microparticles. The term NP refers specifically to a nanoparticle and the term MP refers specifically to a microparticle.

The term "implant," as generally used herein, refers to a polymeric device or element that is structured, sized, or otherwise configured to be implanted, for example by injection or surgical implantation, in a specific region of the body so as to provide therapeutic benefit by releasing one or more active agents over an extended period of time at the site of implantation. For example, intraocular implants may be polymeric devices or elements that are structured, sized, or otherwise configured to be placed in the eye, for example by injection or surgical implantation, and to treat one or more diseases or disorders of the eye by releasing one or more drugs over an extended period. Intraocular implants are generally biocompatible with physiological conditions of an eye and do not cause adverse side effects. Generally, intraocular implants may be placed in an eye without disrupting vision of the eye. The M/NPs of the present disclosure may be contained within implants.

The term "active agent," as used herein, refers to a physiologically or pharmacologically active substance that acts locally and/or systemically in the body. An active agent is a substance that is administered to a patient for the treatment (e.g., therapeutic agent), prevention (e.g., prophylactic agent), or diagnosis (e.g., diagnostic agent) of a disease or disorder. "Ophthalmic Drug" or "Ophthalmic Active Agent", as used herein, refers to an active agent that is administered to a patient to alleviate, delay onset of, or prevent one or more symptoms of a disease or disorder of the eye, or diagnostic agent useful for imaging or otherwise assessing the eye. In particular embodiments, an active agent of the present disclosure is a PPARα agonist.

"Treatment" refers to therapeutic treatments. "Prevention" refers to prophylactic or preventative treatment measures or reducing the onset of a condition or disease. The term "treating" refers to administering the composition to a subject for therapeutic purposes and/or for prevention. Non-limiting examples of modes of administration include oral, topical, retrobulbar, subconjunctival, transdermal, parenteral, subcutaneous, intranasal, intramuscular, intraperitoneal, intravitreal, and intravenous routes, including both local and systemic applications. In addition, the compositions of the present disclosure may be formulated with carrier compounds which provide delayed, controlled, extended, and/or sustained release, for example using formulation techniques which incorporate the active agent into a degradable polymer.

The term "topical" is used herein to define a mode of administration through an epithelial surface, such as but not limited to, a material that is administered by being applied externally to the eye. A non-limiting example of topical administration is through the use of eyedrops, or application of active agent-containing particles.

The terms "therapeutic composition" and "pharmaceutical composition" refer to composition comprising a compound of the present disclosure (also referred to herein as an active agent) that may be administered to a subject by any method known in the art or otherwise contemplated herein, wherein administration of the composition brings about a therapeutic effect as described elsewhere herein. As noted, the compositions of the present disclosure may be designed to provide delayed, controlled, extended, and/or sustained release using appropriate formulation techniques.

The term "effective amount" refers to an amount of an active agent which is sufficient to exhibit a detectable therapeutic or treatment effect in a subject without excessive adverse side effects (such as substantial toxicity, irritation and allergic response) commensurate with a reasonable benefit/risk ratio when used in the manner of the present disclosure. The effective amount for a subject will depend upon the subject's type, size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition or symptom thereof. A detectable or measurable improvement includes a subjective or objective decrease, reduction, inhibition, suppression, limit or control in the occurrence, frequency, severity, progression, or duration of the condition, or an improvement in a symptom or an underlying cause or a consequence of the condition, or a reversal of the condition. A successful treatment outcome can lead to a "therapeutic effect," or "benefit" of ameliorating, decreasing, reducing, inhibiting, suppressing, limiting, controlling or preventing the occurrence, frequency, severity, progression, or duration of a condition, or consequences of the condition in a subject. A decrease or reduction in worsening, such as stabilizing the condition, is also a successful treatment outcome. A therapeutic benefit therefore need not be complete ablation or reversal of the condition, or any single one, most, or all adverse symptoms, complications, consequences or underlying causes associated with the condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition (e.g., stabilizing), over a short or long duration of time (e.g., seconds, minutes, hours).

"Hydrophilic," as used herein, refers to the property of having affinity for water. For example, hydrophilic polymers are polymers which are primarily soluble in aqueous solutions and/or have a tendency to absorb water. In general, the more hydrophilic a polymer is, the more that polymer tends to dissolve in, mix with, or be wetted by water. "Hydrophobic," as used herein, refers to the property of lacking affinity for, or even repelling water. For example, the more hydrophobic a polymer, the more that polymer tends to not dissolve in, not mix with, or not be wetted by water.

Hydrophilicity and hydrophobicity can be spoken of in relative terms, such as, but not limited to, a spectrum of hydrophilicity/hydrophobicity within a group of polymers or polymers. In some embodiments wherein two or more polymers are being discussed, the term "hydrophobic polymer" can be defined based on the polymer's relative hydrophobicity when compared to another, more hydrophilic polymer.

"Biocompatible" and "biologically compatible," as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

"Biodegradable Polymer," as used herein, generally refers to a polymer that will degrade or erode by enzymatic action and/or hydrolysis under physiologic conditions to smaller units or chemical species that are capable of being metabolized, eliminated, or excreted by the subject. The degradation time is a function of polymer composition, morphology, such as porosity, particle dimensions, and environment.

Examples of biodegradable polymers which can be used to form M/NPs of the present disclosure include, but are not limited to, poly (lactide-co-glycolide) (PLGA), as noted above, poly(lactic acid) (PLA), poly(L-lactic acid) (PLLA), poly(glycolic acid) (PGA), poly caprolactone (PCL), poly (lactide-co-caprolactone), poly (glycolide-co-caprolactone), poly (lactide-co-trimethylene carbonate), poly (glycolide-co-trimethylene carbonate), poly (lactide-co-glycolide-co-caprolactone), poly (lactide-co-glycolide-co-trimethylene carbonate), poly-3-hydroxybutyrate, polyanhydrides such as polysebacic anhydride (PSA), and copolymers and mixtures of the above.

Other examples of biodegradable polymers which can be used to form the M/NPs of the present disclosure include, but are not limited to, poly(alkylene glycols), such as polyethylene glycol (PEG). In particular embodiments, the one or more polymers are linear PEG chains. The polymers include, for example, polyethylene glycol block polymers of the polymers listed above, such as poly (lactide-co-glycolide)-block-poly (ethylene glycol) (PLGA-b-PEG), poly (lactide)-block-poly (ethylene glycol) (PLA-b-PEG), and poly(glycolide)-block-poly (ethylene glycol) (PGA-b-PEG). Where used herein, the term PLGA also refers to poly (lactide-co-glycolide).

Representative synthetic polymers which may be used in the M/NPs of the present disclosure thus include poly (hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terephthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxyethyl cellulose, cellulose triacetate, and cellulose sulphate sodium salt (jointly referred to herein as "celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly (octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups, for example, alkyl, alkylene, hydroxylations, oxidations, and other modifications routinely made by those skilled in the art.

Examples of natural polymers which may be used include proteins such as albumin and prolamines, for example, zein, and polysaccharides such as alginate, cellulose and polyhydroxyalkanoates, for example, polyhydroxybutyrate. Examples of non-biodegradable polymers include ethylene vinyl acetate, poly(meth)acrylic acid, polyamides, copolymers and mixtures thereof.

Pharmaceutical formulations of the present disclosure may contain the M/NPs in combination with one or more pharmaceutically acceptable excipients. Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are generally selected from materials which are generally recognized as safe (GRAS), and may be administered to an individual without causing undesirable biological side effects or unwanted interactions.

In some cases, the pharmaceutical formulation of the inner portion of the M/NP contains only one type of polymeric matrix for the controlled release of active agent. In other embodiments, the pharmaceutical formulation of the inner portion contains two or more different types of polymers. Pharmaceutical formulations for ocular administration may be in the form of a sterile aqueous solution or suspension of M/NPs. Acceptable solvents include, for example, water, Ringer's solution, phosphate buffered saline (PBS), and isotonic sodium chloride solution. The formulation may also be a sterile solution, suspension, or emulsion in a nontoxic, parenterally-acceptable diluent or solvent such as 1,3-butanediol. In some instances, the formulation is distributed or packaged in a liquid form. Alternatively, formulations for ocular administration can be packed as a solid, obtained, for example by lyophilization of a suitable liquid formulation. The solid can be reconstituted with an appropriate carrier or diluent prior to administration. Solutions, suspensions, or emulsions for ocular administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers. Solutions, suspensions, or emulsions for ocular administration may also contain one or more tonicity agents to adjust the isotonic range of the formulation. Suitable tonicity agents are well known in the art and some examples include glycerin, mannitol, sorbitol, sodium chloride, and other electrolytes. Solutions, suspensions, or emulsions for ocular administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof. Solutions, suspensions, or emulsions for ocular administration may also contain one or more excipients known art, such as dispersing agents, wetting agents, and suspending agents.

Non-limiting examples of animals or mammals within the scope and meaning of this term include dogs, cats, rats, mice, rabbits, guinea pigs, chinchillas, horses, goats, pigs, cattle, sheep, zoo animals, Old and New World monkeys, non-human primates, and humans.

In at least certain embodiments, the disease and/or condition which can be treated with an M/NP of the present disclosure is characterized by inflammation and/or angiogenesis. Such diseases and/or conditions having an inflammatory basis which can be treated with M/NPs of the present disclosure, include, but are not limited to, inflammatory bowel disease, type 1 or 2 diabetes, insulin resistance, dyslipidemia, Graves disease, multiple sclerosis, various types of arthritis, vasculitis, dermatitis, kidney diseases such as glomerulonephritis, hepatitis, periodontitis, atherosclerosis, hypertension, heart failure, obesity, Alzheimer's disease, and metabolic syndrome, fibrotic disease of the kidney, liver, heart, lung, skin, and gastrointestinal tract, and other disorders and conditions disclosed herein.

Examples of ocular diseases having an inflammatory basis which can be treated with M/NPs of the present disclosure, include, but are not limited to, keratitis, endophthalmitis, blepharitis, conjunctivitis, scleritis, herpetic inflammation, uveitis, vasculitis, arteritis, orbital inflammations, optic neuritis, sympathetic ophthalmia, retinitis, and other autoimmune diseases, age-related macular degeneration, macular edema, diabetic retinopathy, glaucoma, proliferative vitreoretinopathy, corneal edema, uveal edema, and retinal edema. Diseases and/or conditions having an angiogenic basis which can be treated with M/NPs of the present disclosure, include, ocular diseases and/or conditions such as, but not limited to, diabetic retinopathy, age-related macular degeneration, retinopathy of prematurity, retinal artery or vein occlusion, corneal graft rejection, corneal neovascularization, neovascular glaucoma and sickle cell retinopathy, and non-ocular diseases and/or conditions including, but not limited to, cancer, skin diseases, diabetic ulcers, diabetic nephropathy, cardiovascular disease, and stroke.

The M/NPs of the present disclosure can be formed using any suitable method for the formation of polymer microparticles or nanoparticles known in the art. The method employed for particle formation will depend on a variety of factors, including the characteristics of the polymers present in the drug or polymer matrix, as well as the desired particle size and size distribution.

In certain embodiments, as noted above, the particles formed with an active agent contain significant amounts of a coating of an emulsifier on their surfaces. In circumstances where a monodisperse population of particles is desired, the particles may be formed using a method which produces a monodisperse population of nanoparticles. Alternatively, methods producing polydisperse nanoparticle distributions can be used, and the particles can be separated using methods known in the art, such as sieving, following particle formation to provide a population of particles having the desired average particle size and particle size distribution.

Common techniques for preparing microparticles and nanoparticles include, but are not limited to, ultra-sonication, homogenization, solvent evaporation, hot melt particle formation, solvent removal, spray drying, phase inversion, coacervation, and low temperature casting as discussed in more detail below. Pharmaceutically acceptable excipients, including pH modifying agents, disintegrants, preservatives, and antioxidants, can optionally be incorporated into the particles during particle formation.

In solvent evaporation the active agent (or polymer matrix and one or more active agents) is dissolved in a volatile organic solvent, such as methylene chloride. The organic solution containing the active agent is then suspended in an aqueous solution that contains a surface active agent such as PVA. The resulting emulsion is stirred until most of the organic solvent evaporated, leaving solid nanoparticles. The resulting nanoparticles are washed with water and dried overnight in a lyophilizer. Particles with different sizes and morphologies can be obtained by this method. Drugs which contain labile polymers, such as certain polyanhydrides, may degrade during the fabrication process due to the presence of water. For these polymers, the following two methods, which are performed in completely anhydrous organic solvents, can be used.

In solvent removal the active agent (or polymer matrix and one or more active agents) is dispersed or dissolved in a volatile organic solvent such as methylene chloride. This mixture is then suspended by stirring in an organic oil (such as silicon oil) to form an emulsion. Solid particles form from the emulsion, which can subsequently be isolated from the supernatant. The external morphology of spheres produced with this technique is highly dependent on the identity of the drug.

In spray drying, the active agent (or polymer matrix and one or more active agents) is dissolved in an organic solvent such as methylene chloride. The solution is pumped through a micronizing nozzle driven by a flow of compressed gas, and the resulting aerosol is suspended in a heated cyclone of air, allowing the solvent to evaporate from the microdroplets, forming particles. Particles ranging between 0.1-10 microns can be obtained using this method.

In phase inversion, the active agent (or polymer matrix and one or more active agents) is dissolved in a solubilizing solvent, and the solution is poured into a strong non-solubilizing solvent for the active agent to spontaneously produce, under favorable conditions, microparticles or nanoparticles. The method can be used to produce M/NPs in a wide range of sizes, including, for example, about 100 nanometers to about 10 microns, typically possessing a narrow particle size distribution.

Techniques for particle formation using coacervation are known in the art, for example, in U.S. Pat. Nos. 3,266,987, 4,794,000, and 4,460,563. Coacervation involves the separation of an active agent (or polymer matrix and one or more active agents) solution into two immiscible liquid phases. One phase is a dense coacervate phase, which contains a high concentration of the active agent, while the second phase contains a low concentration of the active agent. Within the dense coacervate phase, the active agent forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

Methods for very low temperature casting of controlled release microspheres are described in U.S. Pat. No. 5,019,400. In this method, the active agent (or polymer matrix and active agents) is dissolved in a solvent. The mixture is then atomized into a vessel containing a liquid non-solvent at a temperature below the freezing point of the active agent solution which freezes the active agent droplets. As the droplets and non-solvent for the active agent are warmed, the solvent in the droplets thaws and is extracted into the non-solvent, hardening the microspheres.

In addition to the PPARα agonist active agent present in the polymeric particles, the formulation can contain one or more additional therapeutic, diagnostic, and/or prophylactic agents. The additional agent can be a small molecule or a biomolecule, such as an enzyme or protein, polypeptide, or nucleic acid. Suitable small molecule agents include organic and organometallic compounds. In some instances, the small molecule agent has a molecular weight of less than about 2000 g/mol, or less than about 1500 g/mol, or less than about 1200 g/mol. The small molecule active agent can be a hydrophilic, hydrophobic, or amphiphilic compound. In some cases, the one or more additional agents may be encapsulated in, dispersed in, or otherwise associated in the polymer matrix of the M/NPs.

In the case of pharmaceutical compositions for the treatment of ocular diseases, the formulation may contain one or more ophthalmic drugs. In particular embodiments, the ophthalmic drug is a drug used to treat, prevent or diagnose a disease or disorder of the posterior segment eye. Non-limiting examples of ophthalmic drugs include anti-glaucoma agents, anti-angiogenesis agents, anti-infective agents, anti-inflammatory agents, growth factors, immunosuppressant agents, anti-allergic agents, and combinations thereof. Representative anti-glaucoma agents include prostaglandin analogs (such as travoprost, bimatoprost, and latanoprost), beta-andrenergic receptor antagonists (such as timolol, betaxolol, levobetaxolol, and carteolol), alpha-2 adrenergic receptor agonists (such as brimonidine and apraclonidine), carbonic anhydrase inhibitors (such as brinzolamide, acetazolamine, and dorzolamide), miotics (i.e., parasympathomimetics, such as pilocarpine and ecothiopate), seretonergics muscarinics, dopaminergic agonists, and adrenergic agonists (such as apraclonidine and brimonidine). Representative anti-angiogenesis agents include, but are not limited to, antibodies to vascular endothelial growth factor (VEGF) such as bevacizumab (AVASTIN®) and rhuFAb V2 (ranibizumab, LUCENTIS®), and other anti-VEGF compounds including aflibercept (EYLEA®); MACUGEN® (pegaptanim sodium, anti-VEGF aptamer or EYE001) (Eyetech Pharmaceuticals); pigment epithelium derived factor(s)

(PEDF); COX-2 inhibitors such as celecoxib (CELEBREX®) and rofecoxib (VIOXX®); interferon alpha; interleukin-12 (IL-12); thalidomide (THALOMID®) and derivatives thereof such as lenalidomide (REVLIMID®); squalamine; endostatin; angiostatin; ribozyme inhibitors such as ANGIOZYME® (Sirna Therapeutics); multifunctional antiangiogenic agents such as NEOVASTAT® (AE-941) (Aeterna Laboratories, Quebec City, Canada); receptor tyrosine kinase (RTK) inhibitors such as sunitinib (SUTENT®); tyrosine kinase inhibitors such as sorafenib (Nexavar®) and erlotinib (Tarceva®); antibodies to the epidermal grown factor receptor such as panitumumab (VECTIBIX®) and cetuximab (ERBITUX®), as well as other anti-angiogenesis agents known in the art. Anti-infective agents include antiviral agents, antibacterial agents, antiparasitic agents, and anti-fungal agents. Representative antiviral agents include ganciclovir and acyclovir. Representative antibiotic agents include aminoglycosides such as streptomycin, amikacin, gentamicin, and tobramycin, ansamycins such as geldanamycin and herbimycin, carbacephems, carbapenems, cephalosporins, glycopeptides such as vancomycin, teicoplanin, and telavancin, lincosamides, lipopeptides such as daptomycin, macrolides such as azithromycin, clarithromycin, dirithromycin, and erythromycin, monobactams, nitrofurans, penicillins, polypeptides such as bacitracin, colistin and polymyxin B, quinolones, sulfonamides, and tetracyclines. In some cases, the active agent is an anti-allergic agent such as olopatadine and epinastine. Anti-inflammatory agents include both non-steroidal and steroidal anti-inflammatory agents. Suitable steroidal active agents include glucocorticoids, progestins, mineralocorticoids, and corticosteroids. The ophthalmic drug may be present in its neutral form, or in the form of a pharmaceutically acceptable salt. In some cases, it may be desirable to prepare a formulation containing a salt of an active agent due to one or more of the salt's advantageous physical properties, such as enhanced stability or a desirable solubility or dissolution profile. In some cases, the additional agent is a diagnostic agent imaging or otherwise assessing the eye. Exemplary diagnostic agents include paramagnetic molecules, fluorescent compounds, magnetic molecules, and radionuclides, x-ray imaging agents, and contrast media. In certain embodiments, the pharmaceutical composition contains one or more local anesthetics. Representative local anesthetics include tetracaine, lidocaine, amethocaine, proparacaine, lignocaine, and bupivacaine. In some cases, one or more additional agents, such as a hyaluronidase enzyme, is also added to the formulation to accelerate and improves dispersal of the local anesthetic.

The formulations described herein can be administered locally to the eye by intravitreal injection (e.g., front, mid or back vitreal injection), subconjunctival injection, intracameral injection, injection into the anterior chamber via the temporal limbus, intrastromal injection, injection into the subchoroidal space, intracorneal injection, subretinal injection, and intraocular injection. In some embodiments, the pharmaceutical compositions and/or implants described herein are co-administered with one or more additional agents. "Co-administration", as used herein, refers to administration of the controlled release M/NP formulation with one or more additional agents within the same dosage form, or in separate dosage forms, simultaneously or at essentially the same time. "Essentially at the same time" as used herein generally means within 30 minutes, within 20 minutes, within five minutes, within two minutes, or within in one minute.

As noted above, in some embodiments, the pharmaceutical compositions described herein are co-administered with one or more additional treatments for a neovascular disease or disorder of the eye. In some embodiments, the pharmaceutical compositions described herein are co-administered with one or more anti-angiogenesis agent such bevacizumab (AVASTIN®), ranibizumab, LUCENTIS®, or aflibercept (EYLEA®).

Examples of compounds which can be used as the emulsifier to form the outer coating include, but are not limited to, poly(vinyl alcohol) (PVA), polyethylene oxide-polypropylene oxide-polyethylene oxide polymers (PEO-PPO-PEO), polyoxyethylene sorbitan, surfactants, sucrose esters, and cholic acids. Examples of surfactants include, but are not limited to, Vitamin E-TPGS, sodium dodecyl sulfate, poly(ethylene-alt-maleic anhydride), dioctyl sulfosuccinate sodium, polyoxyl 35 hydrogenated castor oil (e.g., Cremophor EL), polyoxyethylene fatty ether, e.g., polyoxyethylene lauryl ether (e.g., Brij® L23), polyoxyethylene stearyl ether (e.g. Brij® S 100), polyoxyethylene oleyl ether, and olyoxyethylene cetyl ether.

In at least certain embodiments, the weight average Mw of the polymers used herein to contain and/or encapsulate the active agent as M/NPs may be in a kDa range of 2.5, to 3, to 4, to 5, to 10, to 15, to 20, to 25, to 30, to 35, to 40, to 45, to 50, to 55, to 60, to 65, to 70, to 75, to 80, to 85, to 90, to 95, to 100, to 125, to 150, to 175, to 200, to 250, to 300, to 350, to 400, to 450, to 500 kDa. The polymers are at least partially water-soluble such that the contained active agent can be gradually released from the M/NPs. For example, the majority (over 50% to 99%) of the active agent in the M/NPs may be gradually released from the administered M/NPs over a period of from 4 weeks to 12 months, e.g., 8 weeks to 8 months, e.g., 8 weeks to 6 months, e.g., 8 to 32 weeks, e.g., 8 to 16 weeks, e.g., 8 to 12 weeks. The rate of release of the active agent from the M/NPs may be adjusted by altering the ratios of monomer units in the copolymers. For example, in the case of PLGA, degradability of the M/NPs can be decreased by increasing the ratio of lactide (lactic acid) to glycolide (glycolic acid) monomers. Degradation time of the M/NPs can also be extended by endcapping the polymer molecules with esters.

The term "drug loading" (DL) is defined herein as DL % (w/w %)=(amount of fenofibrate in particles)/(weight of particles). In at least certain embodiments, DL % of active agent in the nanoparticles is in the range of about 5% to about 50%, for example about 6% to about 25%.

In addition to the ophthalmic administrations discussed in detail herein above, the therapeutic compositions of the present disclosure may be formulated for administration by any other method known or otherwise contemplated in the art, as long as the route of administration allows for delivery of the active agent(s) so that the compounds can function in accordance with the present disclosure, i.e., as a PPARα agonist. Examples of other routes of administration include, but are not limited to, oral, topical, retrobulbar, subconjunctival, transdermal, parenteral, subcutaneous, intranasal, intramuscular, intraperitoneal, intravitreal, and intravenous routes, including both local and systemic application routes.

Another non-limiting embodiment of the present disclosure is directed to a kit that contain one or more of any of the M/NP compositions described or otherwise contemplated herein. The kit may further contain a second agent as described herein above for use concurrently with the pharmaceutical composition(s). If the composition present in the kit is not provided in the form in which it is to be delivered, the kit may further contain a pharmaceutically (e.g., ophthalmically)-acceptable carrier, vehicle, diluent, excipient, or other agent for mixing with the active agent(s) for preparation of the pharmaceutical composition. The kit including the composition and/or other reagents may also be packaged with instructions packaged for administration and/or dosing of the compositions contained in the kit. The instructions may be fixed in any tangible medium, such as printed paper, or a computer-readable magnetic or optical medium, or instructions to reference a remote computer data source such as a worldwide web page accessible via the internet.

The kit may contain single or multiple doses of the pharmaceutical composition(s). When multiple doses are present, the doses may be disposed in bulk within a single container, or the multiple doses may be disposed individually within the kit; that is, the pharmaceutical compositions may be present in the kit in unit dosage forms to facilitate accurate dosing. The term "unit dosage forms" as used herein refers to physically discrete units suitable as unitary dosages for human subjects and other mammals; each unit contains a predetermined quantity of active material calculated to produce the desired therapeutic effect, in association with a suitable pharmaceutical excipient. Typical unit dosage forms of liquid compositions include prefilled, premeasured ampules or syringes. In such compositions, the M/NPs may sometimes be a minor component (from about 0.1 to about 50% by weight, such as but not limited to, from about 1 to about 40% by weight) with the remainder being various vehicles or carriers and processing aids helpful for forming the desired dosing form. Alternatively, the M/NPs may comprise a major component (>50%) of the compositions.

As is evident from the above, the PPARα agonist-containing M/NPs of the present disclosure can be used for the treatment, inhibition, mitigation, and/or prevention of degenerative retinal disorders, among other diseases and conditions. Thus, certain non-limiting embodiments of the present disclosure include methods of treating, inhibiting, and/or reducing the occurrence of retinal degeneration due to retinal inflammation and neovascularization. One particular but non-limiting embodiment includes a method of treating, inhibiting, and/or reducing the occurrence of one or more pathologic ocular conditions associated with reduced PPARα activity in a subject. In the method, the M/NPs described or otherwise enabled herein are administered to a subject (such as, but not limited to, a mammal) that is experiencing retinal or macular degeneration or that is predisposed to developing retinal or macular degeneration, or other ocular condition or disorder. The M/NPs are administered to the subject in an amount effective to have PPARα agonistic activity in the retina of at least one eye of the subject.

The pathologic ocular condition may be any of the conditions described herein, and the pathologic ocular condition may be characterized by retinal and/or macular degeneration. In one embodiment, the M/NPs may be administered topically to an eye of the subject (such as, but not limited to, as an eyedrop). In an alternative embodiment, the pharmaceutical composition may be administered by ocular injection (e.g., IVT), or systemically.

The amount of the M/NPs that is effective in the treatment described herein can be determined by the attending diagnostician, as one of ordinary skill in the art, by the use of conventional techniques and by observing results obtained under analogous circumstances. For example, in one non-limiting embodiment of a treatment, in determining the therapeutically effective dose, a number of factors may be considered by the attending diagnostician, including, but not limited to: the species of the subject; its size, age, and general health; the specific disease and/or condition involved; the degree, involvement, and/or severity of the disease and/or condition; the response of the individual subject; the particular active agent(s) or other therapeutic compound(s) administered; the mode of administration; the bioavailability characteristics of the preparation administered; the dose regimen selected; the use of concomitant medication; and other relevant circumstances. A therapeutically effective amount of a pharmaceutical composition of the present disclosure also refers to an amount of the active agent(s) which is effective in controlling and/or reducing or ameliorating the disease and/or condition.

For example, but not by way of limitation, the therapeutically effective amount of M/NPs used in the present disclosure will generally contain sufficient active agent (e.g., a fibrate such as fenofibrate, pemafibrate, or other fibrate, or other PPARα agonist) to deliver in a range of from about 0.01 µg/kg to about 10 mg/kg (weight of active ingredient/body weight of patient). For example, but not by way of limitation, the composition will deliver about 0.1 µg/kg to about 10 mg/kg, or about 1 µg/kg to about 10 mg/kg, or about 1 mg/kg to about 10 mg/kg, or about 0.01 µg/kg to about 5 mg/kg, or about 0.1 µg/kg to about 5 mg/kg, or about 1 µg/kg to about 1 mg/kg, or about 10 µg/kg to about 10 mg/kg, or about 100 µg/kg to about 10 mg/kg, or about 10 µg/kg to about 1 mg/kg.

Practice of the method of the present disclosure may include administering to a subject a therapeutically effective amount of the pharmaceutical composition (containing the active agent(s)) in any suitable systemic and/or local formulation, in an amount effective to deliver the dosages listed above. The dosage can be administered, for example, but not by way of limitation, on a one-time basis, or administered at multiple times (for example, but not by way of limitation, from one to 12 times per year). The pharmaceutical composition may be administered either alone or in combination with other therapies, in accordance with the inventive concepts disclosed herein.

EXAMPLES

Certain embodiments of the present disclosure will now be discussed in terms of several specific, non-limiting, examples. The examples described below will serve to illustrate the general practice of the present disclosure, it being understood that the particulars shown are merely exemplary for purposes of illustrative discussion of particular embodiments of the present disclosure only and are not intended to be limiting of the claims of the present disclosure.

Example 1

Nanoparticles comprising fenofibrate and PLGA of various Mw were formulated. Fenofibrate-NPs made of 34 kDa Mw PLGA (Feno-NP$_{PLGA34kDa}$) with a lactide/glycolide ratio of 1:1, were selected for detailed experimental analysis and demonstrated a drug content of 6% w/w (fenofibrate:PLGA) and a sustained drug release up to at least 60 days in vitro. In one in vivo experiment, rats were given a single intravitreal (IVT) injection of the Feno-NP$_{PLGA34kDa}$ into the eyes with a 30G fine needle. Fenofibric acid drug levels in the eye were sustained for more than 60 days. The efficacy of the Feno-NPs for DR and neovascular AMD was investigated using streptozotocin (STZ)-induced diabetic rats, laser-induced choroidal neovascularization (CNV) rats, and very low-density lipoprotein receptor knockout (Vldlr$^{-/-}$) mice. Therapeutic effects of the PLGA 34 kDa Feno-NPs were evaluated by measuring electroretinogram (ERG), retinal vascular leakage, leukostasis, CNV size, and retinal levels of vascular endothelial growth factor (VEGF) and intracellular adhesion molecule-1 (ICAM-1) in the test animals. In the diabetic rats, Feno-NPs ameliorated retinal dysfunctions, reduced retinal vascular leakage, inhibited retinal leukostasis, and downregulated the overexpression of VEGF and ICAM-1 at 8 weeks after one IVT injection. In addition, Feno-NPs reduced retinal vascular leakage and CNV formation in both CNV rats and Vldlr$^{-/-}$ mice. Feno-NPs exhibited good physiochemical characteristics and controlled drug release profile, conferring prolonged beneficial effects on DR and neovascular AMD.

Methods

Materials. PLGAs (LA:GA ratio 50:50, acid terminated) with Mw of 5, 18, 34 and 54 kDa (PLGA 5 kDa, PLGA 18 kDa, PLGA 34 kDa, PLGA 54 kDa) were purchased from Evonik Corporation (Birmingham, Ala.). Fenofibrate, Tween 80, streptozotocin, Evans blue, FITC-dextran ($2\times10^6$ molecular mass, fixable), FITC-conjugated concanavalin-A, mouse anti-β-actin antibody and organic solvents were purchased from Sigma-Aldrich (St. Louis, Mo.). Poly(vinyl alcohol) (PVA) solution (Mw=25 kDa with 88% hydrolysis) was purchased from Polysciences (Warrington, Pa.). Ketamine hydrochloride and xylazine were purchased from Vedco (St. Joseph, Mo.), and cyclopentolate (1%) was purchased from Wilson (Mustang, Okla.).

Preparation of Feno-NPs. NPs were prepared using an emulsification method wherein 50 mg PLGA with different molecular weight and 10 mg fenofibrate were fully dissolved in 1 mL dichloromethane (DCM). The oil phase was emulsified in 5 mL 1% PVA solution in an ice-water bath using a probe sonicator (VibraCell, Sonics & Materials Inc., Newtown, Conn.) with a one-eighth inch stepped microtip under 30% amplitude for 2 min. This emulsion was poured into another 40 mL aqueous phase 0.3% PVA solution under magnetic stirring at 700 rpm for at least 3 hours to allow solvent to evaporate. The solvent was further evaporated by placing the solution in a vacuum chamber for 30 min. The final nanoparticle suspensions were filtered through a 0.7 μm GF/F syringe filter to remove any drug crystals before centrifugation at 8,000×g for 25 min, and thoroughly washed with DI water. The final Feno-NPs were resuspended in ultrapure water, and one drop of the suspension was applied on glass slide to check whether there were drug crystals using an optical microscope. Blank PLGA NPs (Blank-NPs) were prepared using the same method, and no fenofibrate was dissolved in the DCM solution. The fresh Blank-NPs and Feno-NPs were directly used for the following animal studies. A small volume (25 μL) of Feno-NPs were lyophilized for the measurement of drug loading.

Nanoparticle Physiochemical Characterization. Particle size, polydispersity index (PDI) and surface charge of the Feno-NPs were determined using a Zetasizer Nano ZS90 (Malvern Instruments, Southborough, Mass.). NPs were suspended in 10 mM NaCl solution (pH 7.2). Nanoparticle morphology was characterized using transmission electron microscope (TEM) (Jeol JEM-1230, JEOL Ltd., Tokyo, Japan).

Drug Loading and In Vitro Drug Release Study. The 25 μL lyophilized Feno-NPs were weighed, dissolved in 1 mL acetonitrile (ACN), and the solution was measured by HPLC after filtering through a 0.22 μm PTFE syringe filter. Isocratic separation was performed on a Shimadzu Prominence LC system equipped with a Pursuit 5 C18 column and mobile phase consisting of acetonitrile/water (80/20 v/v) containing 0.1% trifluoroacetic acid (flow rate=1 mL/min). Column effluent was monitored by UV detection at 285 nm. The fenofibrate concentration was calculated using an established standard curve. The encapsulation efficiency (EE) is calculated as EE (%)=(actual drug loading)/(theoretical drug loading).

To measure the in vitro release profile of fenofibrate, 400 μL of the Feno-NP suspension (~4 mg NPs) was sealed in a dialysis tubing cellulose membrane (Mw cutoff: 14 kDa, Sigma Aldrich, St. Louis, Mo.). The sealed dialysis membrane was placed into a 50 mL conical tube containing 12 mL of release media (0.2% tween 80 in PBS, pH 7.4) and incubated at 37° C. on a platform shaker (140 rpm). Tween 80 is used to increase the solubility of fenofibrate, and the solubility of fenofibrate in the release medium was measured to be 9.4 μg/mL. The entire release media was collected at predetermined intervals and replaced with another 12 mL of fresh 0.2% Tween 80 PBS solution. Sample collection and release medium replacement was carried out at 2 h, 4 h, 8 h, 24 h in the first day, daily during the first week, and then every other day throughout the whole 2 months. The release experiments were conducted in triplicate. Fenofibrate concentration in the collected release media was measured by HPLC.

Animals. Male Brown Norway (8 weeks old, Charles River, Wilmington, Mass.) and Vldlr$^{-/-}$ mice (Jackson Laboratory, Bar Harbor, Me.) were used in this study. Care, use, and treatment of the animals were in agree with the ARVO Statement for the Use of Animals in Ophthalmic and Vision Research, and local ethics committee approval was obtained. In all procedures, animals were anesthetized with an intramuscular injection of 50 mg/kg ketamine hydrochloride mixed with 5 mg/kg xylazine, and pupils were dilated with topical administration of 1% cyclopentolate.

Measurement of Fenofibric Acid in Eyecups of Rats. Five microliters of Feno-NPs (30 μg fenofibrate) were injected into the vitreous of Brown Norway rats with a 30G needle. At day 4, 7, 14, 30 and 60 days after the injection, rats were sacrificed and their eyecups containing vitreous, retina, choroid, and sclera, were obtained and stored at−80° C. until assay. Fenofibrate exerts therapeutic effects only after it is converted to fenofibric acid by hydrolysis of the ester bond by esterase, which exists in plasma and tissues including ocular tissues. In order to detect only active drug levels released from Feno-NPs, we measured fenofibric acid in the eyecups using LC-MS/MS. In brief, the eyecup was homogenized in 300 μL water with a Fasprep96 homogenizer (MP Biomedicals, LLC.). Tissue homogenate was diluted in acetone and an internal standard (ketoprofen) was added, and then centrifuged at 5,000×g for 5 min at 4° C. The supernatant was collected and then transferred to a preconditioned SPE (Thermofisher). Following the loading of 200 μL of supernatant, the plate was washed with 200 μL of water with EDTA, and 200 μL of methanol. A collection plate was then placed under the SPE plate, and 2×75 μL of methanol was used for elution. This eluent was then injected into the LC-MS/MS. Analysis was performed using an API 4000 mass spectrometer (AB Sciex) coupled to a Nexerax2 UHPLC system (Shimadzu Corporation). Fenofibric acid and ketoprofen were separated using a Thermo Accucore C18 column (50 mm×2.1 mm). The mobile phase was methanol/H$_2$O (80:20) containing 0.1% formic acid (flow rate is 0.3 mL/min). The column temperature was maintained at 40° C. The MS detector was operated in multiple reaction monitoring (MRM) mode at unit mass resolution with a dwell time of 100.0 ms for all test compounds. The optimized mass spectrometric parameters, MRM transitions for fenofibrate and fenofibric acid are m/z 361.0 to 121.0 in positive ESI mode and m/z 319.0 to 232.9 in negative ESI mode, respectively. Data were acquired and analyzed using Analyst software version 1.4 (Applied Biosystems). Mean concentration time curve was used for pharmacokinetics analysis. The peak tissue concentration ($C_{max}$) and the time to reach $C_{max}$ ($T_{max}$) were calculated.

Efficacy of Feno-NPs on DR in STZ-Induced Diabetic Rats. Diabetes was induced by STZ injection (see Chen, Y.; Hu, Y.; Lin, M.; Jenkins, A. J.; Keech, A. C.; Mott, R.; Lyons, T. J.; Ma, J. X., Therapeutic effects of PPARalpha agonists on diabetic retinopathy in type 1 diabetes models. Diabetes 2013, 62 (1), 261-72). Blood glucose levels were measured 3 days after the STZ injection and monitored weekly thereafter. Only animals with consistently elevated glucose levels>350 mg/dL were considered diabetic. One month after STZ injection, a single IVT injection of 5 μL Blank-NPs (0.5 mg NPs) or Feno-NPs (30 μg fenofibrate) was given. Eight weeks after the IVT injection, the effects of Feno-NPs on DR were evaluated by measuring retinal function, retinal vascular leakage, retinal leukostasis, and the expression levels of VEGF and ICAM-1.

Efficacy of Feno-NPs on Laser-Induced CNV in Rats. CNV was induced by laser photocoagulation. Laser parameters were 532 nm of wavelength, 75 μm of spot size, 100 milliseconds (ms) of exposure time, and 500 mW of power. Eight spots were applied in each eye. Only burns that generated a bubble, indicating the rapture of Bruch's membrane, were included in the study. A single IVT injection of 5 μL Blank-NPs (0.5 mg NP) or Feno-NP (30 μg fenofibrate) was given immediately after laser injury. Vascular leakage and CNV size were measured after two weeks.

Efficacy of Feno-NPs on Ocular NV in Vldlr$^{-/-}$ Mice. A single IVT injection of 1.5 μL Blank-NPs (150 μg NPs) or Feno-NPs (9 μg fenofibrate) was given to Vldlr$^{-/-}$ mice at age of P21. One month after the injection, vascular leakage was measured, and numbers of subretinal NV (SRNV) and intra-retinal NV (RNV) lesions were counted in choroidal and retinal flat mount, respectively.

Toxicities of Blank-NPs and Feno-NPs to the Structure and Function of the Retina in Healthy Rats. A single IVT injection of 5 μL Blank-NPs (0.5 mg NP) or Feno-NPs (30 μg fenofibrate) was performed in normal rats. Retinal function was examined at 2 weeks and 4 weeks post injection, and retinal structure was examined at 4 weeks post injection.

Electroretinogram (ERG) Recording. ERG was recorded using Diagnosys Espion Visual Electrophysiology (Lowell, Mass.). Briefly, rats were dark adapted overnight. ERG was elicited by flash stimuli delivered with a Ganzfeld photostimulator. The a- and b-wave amplitudes in both eyes were recorded and analyzed.

Optical Coherence Tomography (OCT). A SD-OCT device (Bioptigen Inc. Durham. N.C., USA) was used to record the ERG. Images were captured with rectangular scan at 1000 A-scans per B-scan, and 100 B-scans per frame. Total retinal thickness (TRT) was measured perpendicular to the surface of retinal pigment epithelial (RPE) layer and retinal nerve fiber layer (RNFL) at 12, 3, 6, and 9 o'clock positions, 500 μm away from the center of optic nerve head (ONH) using the built-in software (InVivoVU, Bioptigen), and then averaged. The examiners were blinded to the treatment information.

Retinal Vascular Permeability Assay. Retinal vascular permeability was measured using the Evans blue (30 mg/kg) as a tracer.

Retinal Vascular Leukostasis Assay. The adherent leukocytes in the retinal vasculature were stained by perfusion with FITC-conjugated concanavalin-A (200 μg/ml). The number of adherent leukocytes in the retinal artery, vein and their first-grade branches in the whole retina were counted.

Western Blot Analysis. Western blot analysis was performed. Individual protein bands were semi-quantified by densitometry using ImageJ and normalized by β-actin levels. Rabbit anti-VEGF antibody (Abcam, Cat #ab46154; Cambridge, Mass., goat anti-ICAM-1 antibody (Abcam, Cat #ab27536; Cambridge, Mass.), and mouse anti-β-actin antibody (Sigma-Aldrich, Cat #A5441; St. Louis, Mo.) were used.

Fundus Photography (FP) and Fundus Fluorescein Angiography (FFA). FP and FFA were performed as described in Qiu et al. 2017 (Qiu, F.; Matlock, G.; Chen, Q.; Zhou, K.; Du, Y.; Wang, X.; Ma, J.-X., Therapeutic Effects of PPARα Agonist on Ocular Neovascularization in Models Recapitulating Neovascular Age-Related Macular Degeneration. Invest. Ophth. Vis. Sci. 2017, 58 (12), 5065-5075). For CNV rats, images were captured at 1 and 5 min after the i.p. injection of fluorescein solution, and fluorescein leakage was graded (Table 1). For Vldlr$^{-/-}$ mice, fluorescein leakage spots were quantified at 5 min after the injection.

TABLE 1

Evaluation of fluorescein leakage in CNV rats (grade 0-3).

| Clinical parameter | Grade | | | |
|---|---|---|---|---|
| | 0 | 1 | 2 | 3 |
| Leakage | None | Questionable | Leaky | Pathologically significant leaky |
| Hyper-fluorescence intensity | Faint or speckled | No advancing increase | Increase | Increase |
| Hyper-fluorescence size | None | No advancing increase | Not significant increase, no definite leakage | Increase with definite leakage |

Choroidal and Retinal Flat Mount Stained with FITC-Dextran (FITC-D). Fixable FITC-D (20 mg/mL, 10 mL/kg) was injected into anesthetized animals through the femoral vein. The animals were sacrificed at 5 mins after FITC-D injection and the eyes were enucleated and fixed in 4% paraformaldehyde for 2 hours. The retina and eyecup were flat-mounted separately on slides, and fluorescent images were captured. NV areas or numbers were measured with the ImageJ software.

Statistical Analysis. Statistical analysis was performed using SPSS 15.0 software (SPSS, Chicago, Ill.). Values were expressed as n (%) or mean±standard error of mean (SEM). Categorical variables were compared using the Chi-square ($x^2$) test. Quantitative data were analyzed using one or two-way analysis of variance (ANOVA) followed by Bonferroni post hoc tests. $P<0.05$ was considered statistically significant.

Results

Characteristics of Feno-NPs. Fenofibrate was encapsulated into PLGA NPs with different Mw PLGA polymers using the emulsification method. The physicochemical properties of Feno-NPs are shown in Table 2. All Feno-NPs were monodispersed (PDI<0.1), had particle size around 250 nm and possessed a spherical shape (FIG. 1A). Feno-NPs exhibited a nearly neutral surface charge, contributed by the PVA coating on NP surface. The PVA coatings can further stabilize the feno-NPs, prevent particle aggregation, and allow smooth IVT injection of Feno-NPs through fine gauge needles. There were no drug crystals in Feno-NP suspensions after filtering and washing. Drug loading in Feno-NP increased with the molecular weight of PLGA (Table 2). Relatively high Mw PLGA 34 kDa and PLGA 54 kDa achieved high drug loading of 6% and 7.9% w/w, respectively, corresponding to an encapsulation efficiency of 36% and 47%. There were also no drug crystals when PLGA 34 kDa and PLGA 54 kDa were used to formulate Feno-NPs. While PLGA 18 kDa and PLGA 5 kDa were used, the drug loading was reduced to 4.1% and 1.1%, respectively. We observed numerous drug crystals in Feno-NPs made with PLGA 18 kDa and PLGA 5 kDa before filtering (data not shown), indicating a poor drug encapsulation in NPs of lower molecular weight PLGA.

TABLE 2

Physicochemical Properties of NPs

| Polymer | Particle size (nm) | PDI | ζ-potential (mV) | Drug loading (wt. %) | EE (%) |
|---|---|---|---|---|---|
| PLGA 5kDa | 224 ± 12 | 0.03 ± 0.02 | −6 ± 4 | 1.1 | 6.6 |
| PLGA 18kDa | 250 ± 12 | 0.03 ± 0.01 | −1.5 ± 0.5 | 4 | 24 |
| PLGA 34kDa | 265 ± 10 | 0.03 ± 0.01 | −1.2 ± 0.1 | 6 | 36 |
| PLGA 54kDa | 252 ± 4 | 0.05 ± 0.03 | −1 ± 0.2 | 7.9 | 47 |

Figure 1B:
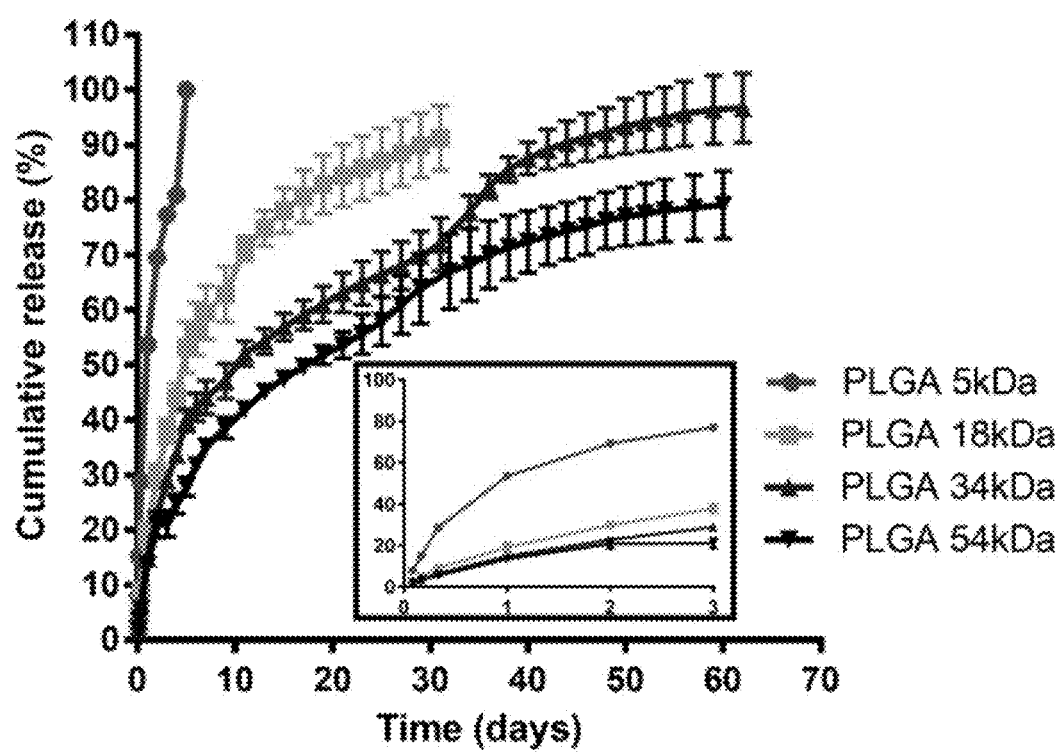
FIG. 1B shows an in vitro drug release profiles of Feno-NPs made of PLGA of 5 kDa, 18 kDa, 34 kDa and 54 kDa. The insert shows an expanded drug release profile during the first 3 days.

Fenofibrate was released from Feno-NPs in a controlled manner under sink conditions in vitro (FIG. 1B). The drug release rate from Feno-NPs was significantly affected by the molecular weight of PLGA. Quick drug release with an obvious burst release was observed when PLGA 5 kDa was used for Feno-NPs, and 100% of drug was released within 1 week. Feno-NPs prepared with PLGA 18 kDa and 34 kDa demonstrated a longer-lasting drug release profile in a controlled manner ranging from 1 month to 2 months, respectively, without obvious initial burst release (FIG. 1B). Feno-NPs made of PLGA 54 kDa only released~70% of loaded drug by 2 months, demonstrating a slow release lasting much longer than 2 months. The drug release profiles for PLGA 34 kDa and PLGA 54 kDa appeared to be tri-phasic with a first order release during the first month and a short-period rapid release, followed by another gradual drug release to reach plateau. The rapid release around 1 month could be attributed to the degradation of PLGA 34 kDa and PLGA 54 kDa in Feno-NPs allowing the rapid diffusion of fenofibrate. Based on the drug release profiles and the animal efficacy study timeframe (~2 months), Feno-$NP_{PLGA34kDa}$ were selected for following efficacy and toxicity studies as they provide continuous drug release for approximately 2 months in vitro.

Figure 2:
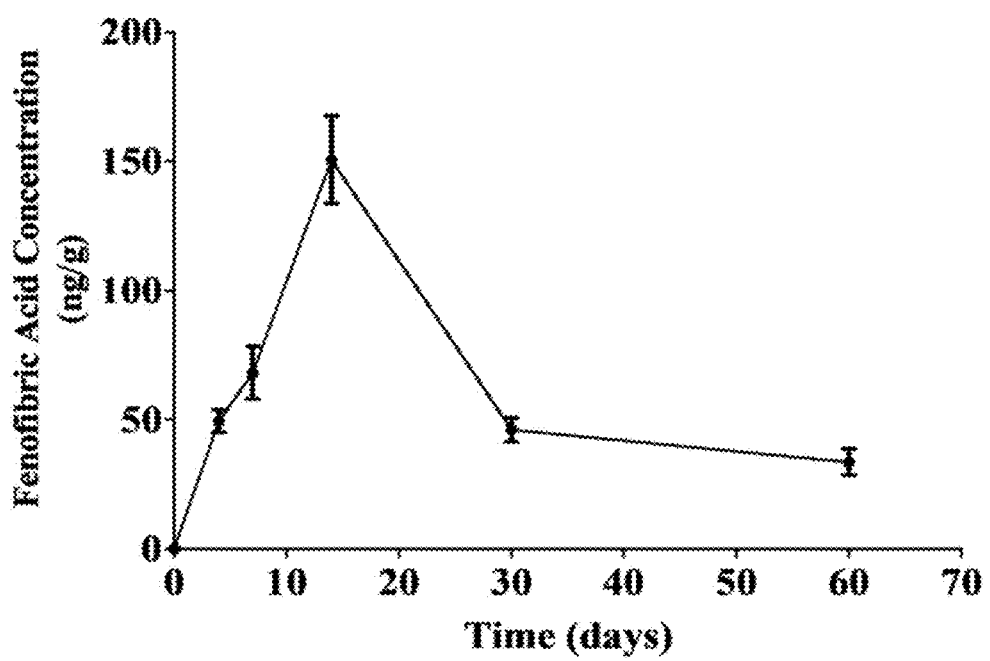
FIG. 2 shows the pharmacokinetics of Feno-NP$_{PLGA34kDa}$ based on fenofibric acid concentration in the eyecup tissue containing vitreous, retina, choroid, and sclera. Means±SEM (n=4).

Ocular Pharmacokinetics of Feno-NPs. The determination of released drug levels in ocular tissues was carried out in BN rats after a single IVT injection of Feno-NPs. In order to remove the influence from NP-encapsulated fenofibrate to the released drugs, we measured fenofibric acid, the parent drug after the conversion from released fenofibrate. The fenofibric acid levels in the eyecup during 2 months were measured by LC-MS/MS and the profile was shown in FIG. 2. The calculated $T_{max}$ was 14 days and $C_{max}$ was 150.5 ng/g. One single IVT injection of Feno-NPs provided a sustained level of fenofibric acid for at least 60 days in the eye, and fenofibric acid concentration at 60 days was 33.6±5.1 ng/g eyecup.

Figure 3A:
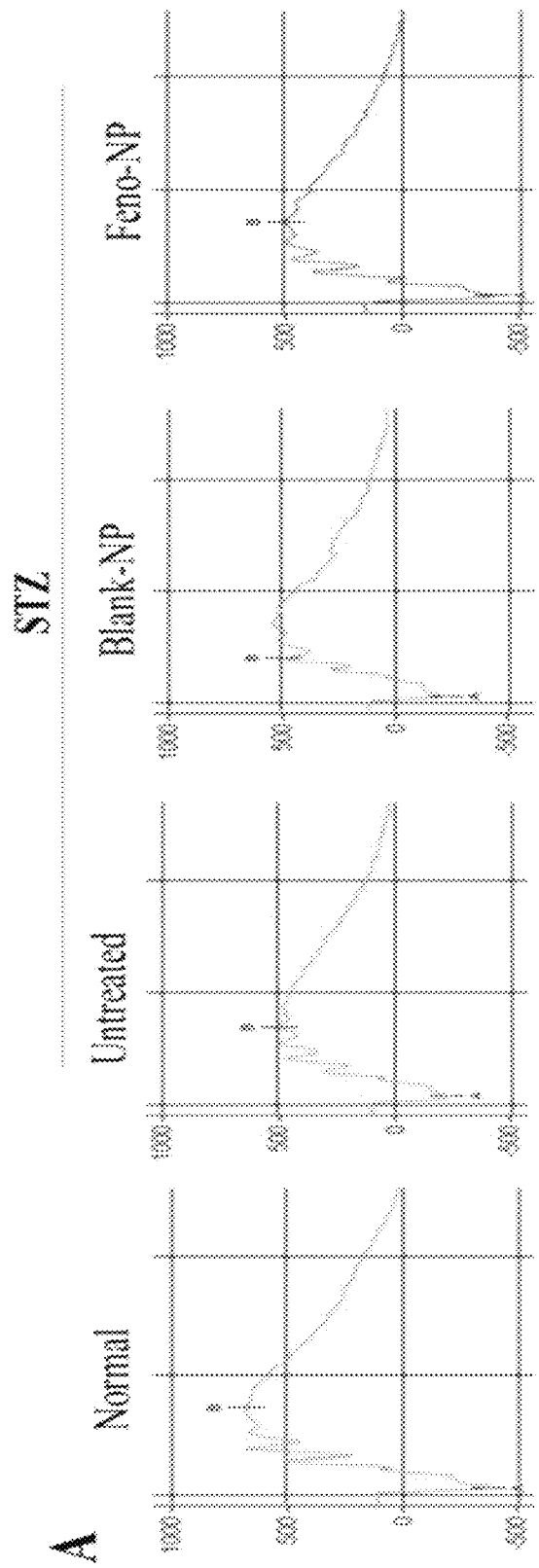
FIG. 3A shows representative electroretinography (ERG) waveforms in normal rats, untreated diabetic rats, Blank-NP treated STZ-induced diabetic rats, and Feno-NP (Feno-NP$_{PLGA34kDa}$)-treated STZ-induced diabetic rats.
Figure 3B:
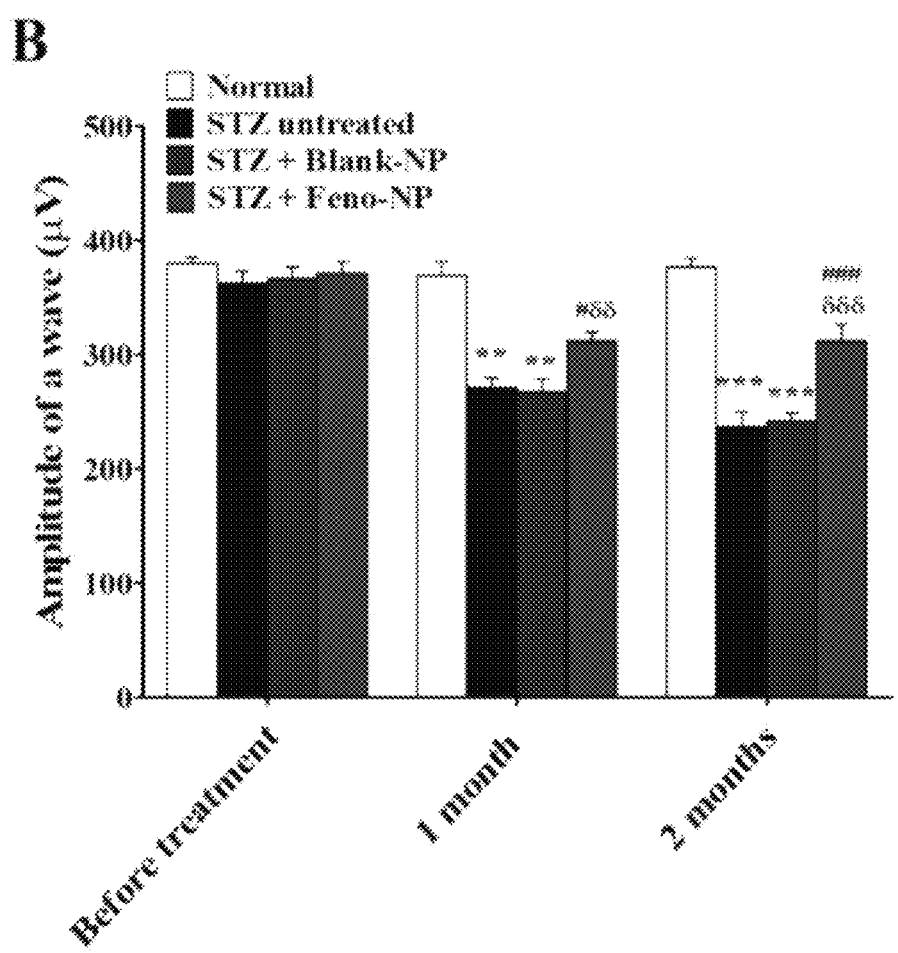
FIG. 3B shows the effect of Feno-NP$_{PLGA34kDa}$ on retinal function with ERG in STZ-induced diabetic rats. Quantification of amplitude of "a" wave on scotopic ERG measured at intensity of 600 cd. s/m². Mean±SEM (n=10-12/group). Two-way ANOVA followed by Bonferroni post hoc test.  $P<0.01$, versus normal rats; * $P<0.001$, versus normal rats. #$P<0.05$, versus untreated diabetic rats; ##$P<0.01$, versus untreated diabetic rats; ###$P<0.001$, versus untreated diabetic rats, δδ $P<0.01$, versus Blank-NP treated diabetic rats; δδδ $P<0.001$, versus Blank-NP treated diabetic rats.
Figure 3C:
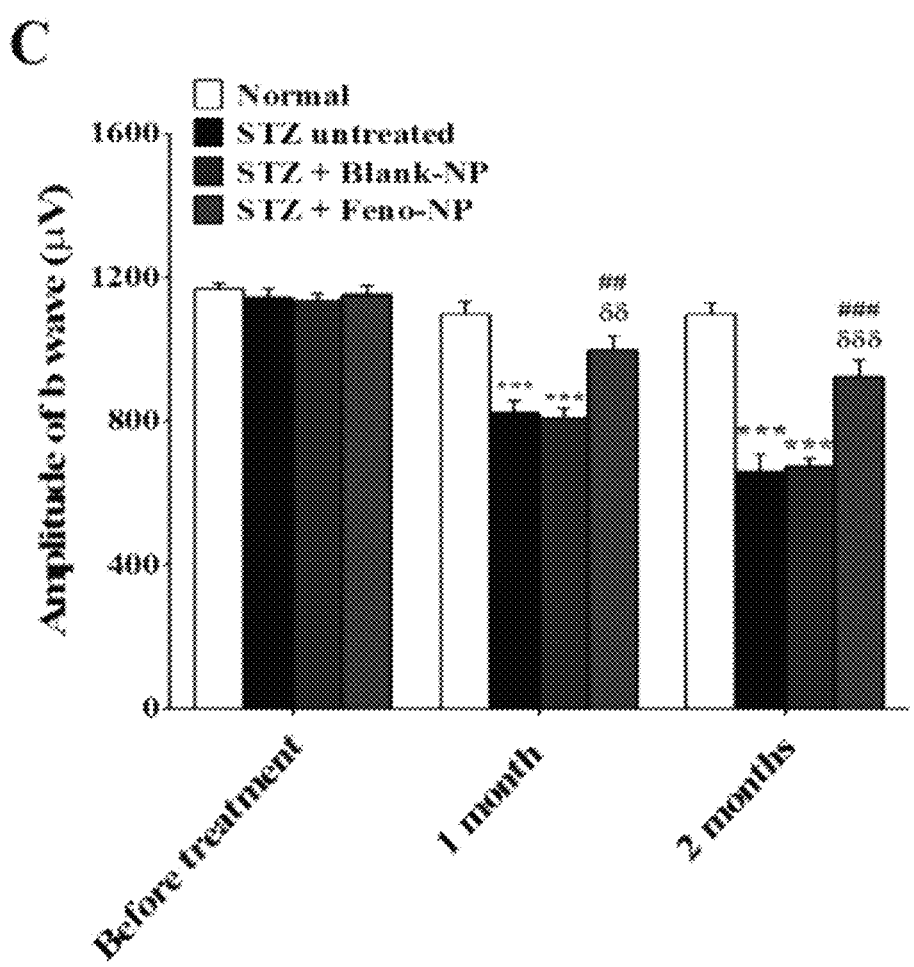
FIG. 3C shows the effect of Feno-NP$_{PLGA34kDa}$ on retinal function with ERG in STZ-induced diabetic rats. Quantification of amplitude of "b" wave on scotopic ERG measured at intensity of 600 cd. s/m$^2$. Mean±SEM (n=10-12/group). Two-way ANOVA followed by Bonferroni post hoc test.  P<0.01, versus normal rats; * P<0.001, versus normal rats. #P<0.05, versus untreated diabetic rats; ##P<0.01, versus untreated diabetic rats; ###P<0.001, versus untreated diabetic rats, δΔ P<0.01, versus Blank-NP treated diabetic rats; δδδ P<0.001, versus Blank-NP treated diabetic rats.

A Single IVT Injection of Feno-NPs Improves Retinal Function in STZ-Induced Diabetic Rats. Retinal dysfunction, as shown by declined ERG a- and b-wave amplitudes in DR patients and diabetic animals, is one of the signs of DR, and also the target of treatment for DR. The results demonstrated that both a-wave and b-wave amplitudes of scotopic ERG were decreased in STZ-induced diabetic rats, compared with non-diabetic rats. A single IVT injection of Feno-NPs partially normalized the ERG decline, at 4 and 8 weeks after the injection, compared with diabetic rats without treatment or diabetic rats with injection of the same amount of Blank-NPs (FIG. 3), indicating that Feno-NP has a protective effect against the retinal function impairment induced by diabetes, and this effect can last for at least 8 weeks. We also observed that the NP were still visible in the posterior chamber under fundus photography until 6 weeks (data not shown). However, these diabetic rats developed severe cataract from 2 months after onset of diabetes, subsequently, blocking the visual pathway and preventing further monitoring of NP in the posterior chamber.

Figure 4A:
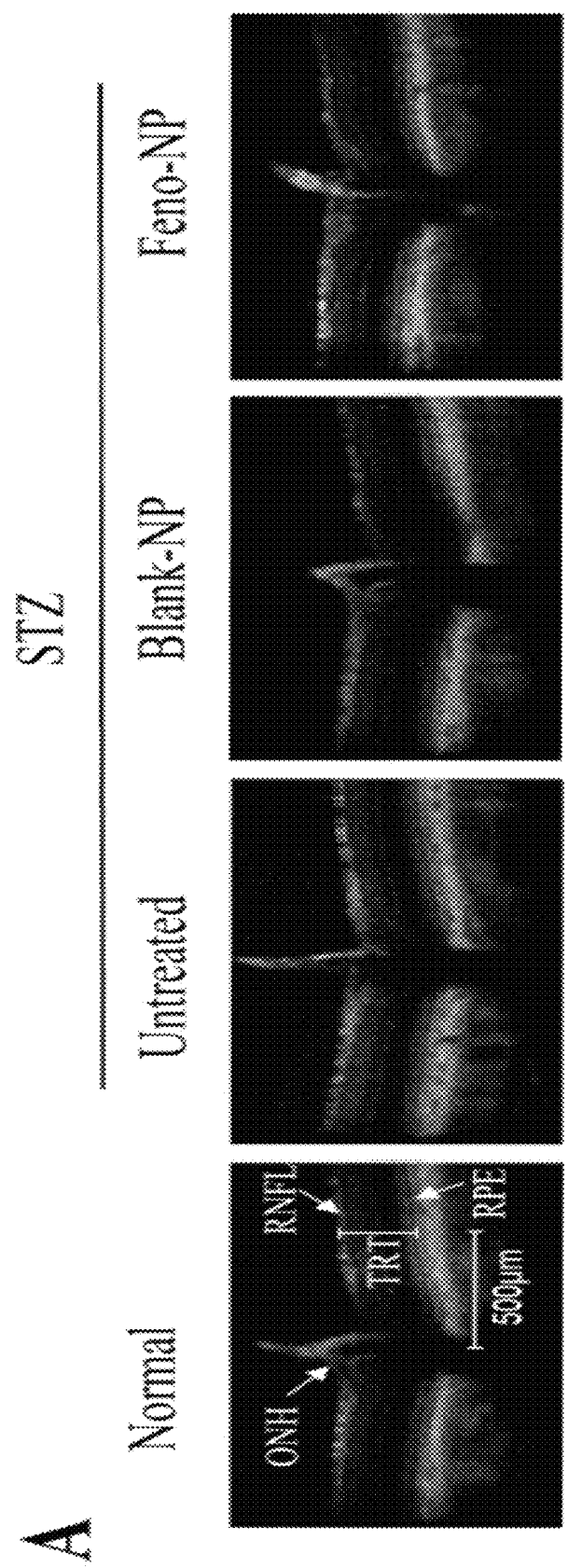
FIG. 4A shows representative images of optical coherence tomography (OCT) of the effect of Feno-NP$_{PLGA34kDa}$ on retinal vascular leakage and retinal edema in STZ-induced diabetic rats. Retinal edema was evaluated by total retinal thickness using OCT 2 and 4 weeks after Feno-NP treatment, and retinal vascular leakage was measured by permeability assay 8 weeks after Feno-NP treatment.
Figure 4B:
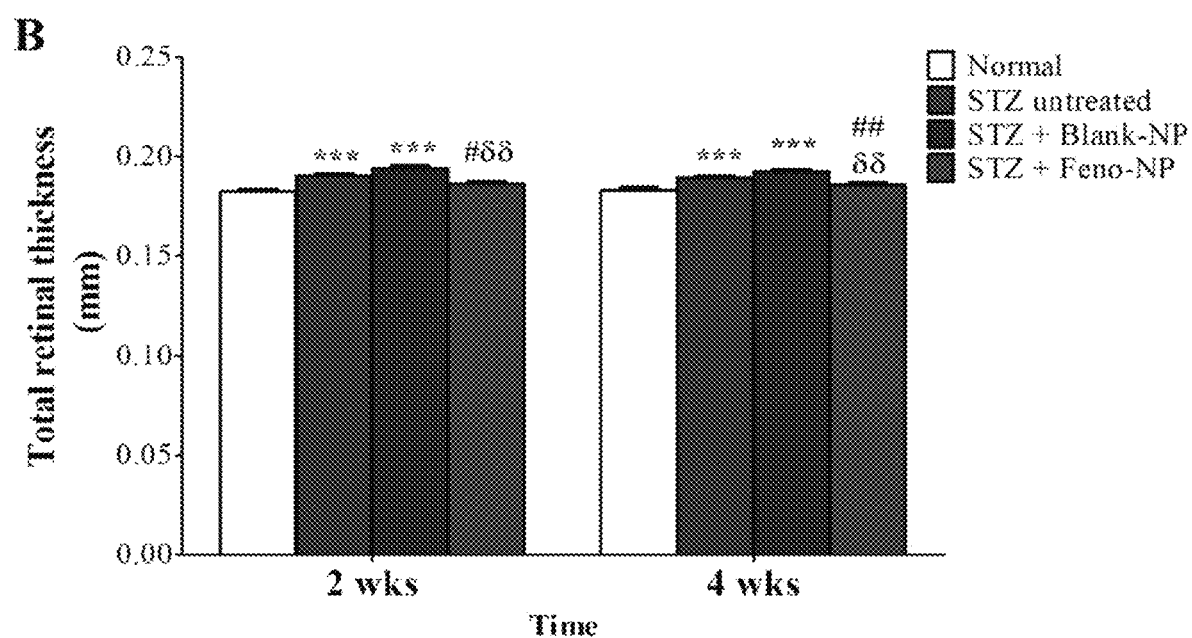
FIG. 4B shows quantification of total retinal thickness (n=12/group) on OCT in the rats of FIG. 4A. TRT: total retinal thicknesses; RPE: retinal pigment epithelial layer; RNFL: retinal nerve fiber layer (RNFL); ONH: optic nerve head (ONH).
Figure 4C:
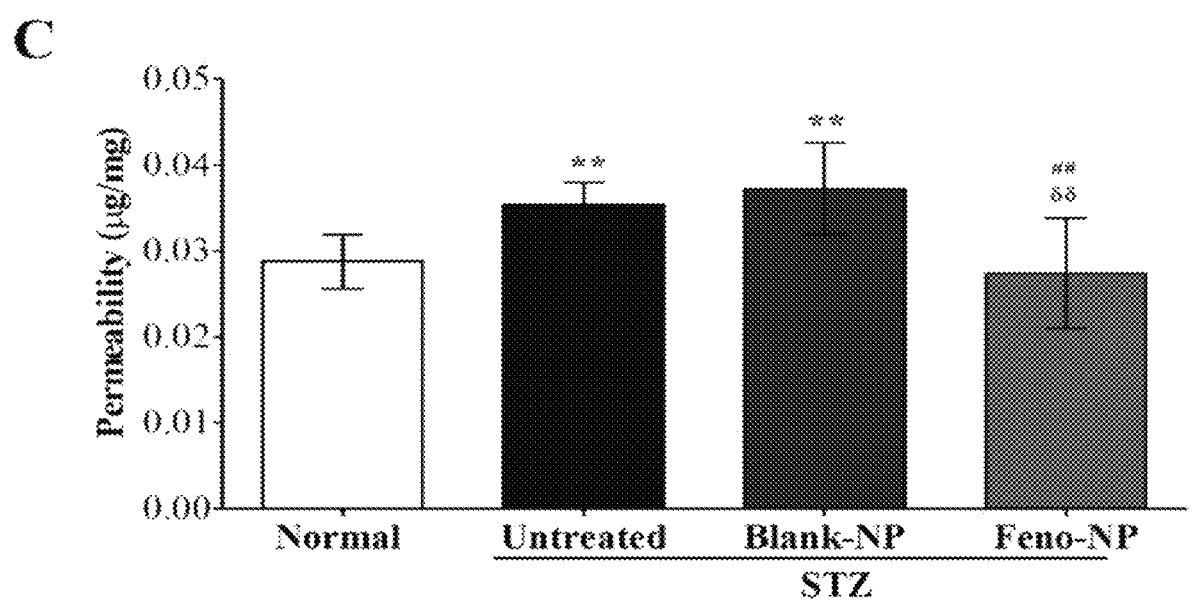
FIG. 4C shows quantification of permeability (n=12/group) in the rats of FIG. 4A. Mean±SEM. Two-way ANOVA followed by Bonferroni post hoc test.  P<0.01, versus normal rats; * P<0.001, versus normal rats. ##P<0.01, versus untreated diabetic rats. δδ P<0.01, versus Blank-NP treated diabetic rats.

A Single IVT Injection of Feno-NPs Attenuates Retinal Vascular Leakage and Retinal Edema in STZ-Induced Diabetic Rats. Retinal vascular leakage, a common pathological feature in DR, which can occur or reoccur at any stage of DR, is a major cause of macular edema and loss of vision in diabetic patients. In the present disclosure, total retinal thickness was increased in diabetic rats, compared with normal rats as shown by OCT (FIG. 4A, B), demonstrating retinal edema. This result was consistent with the increased retinal vascular permeability in diabetic rats, compared with normal rats (FIG. 4C). A single IVT injection of Feno-NPs, but not Blank-NPs, prevented the increase of retinal thickness in diabetic rats and reduced the retinal vascular permeability at 8 weeks post injection, compared with diabetic rats without treatment, to a level similar to nondiabetic rats (FIG. 4A-C). It is comparable to the effects achieved via oral administration daily in prior work. These results indicate that a single injection of Feno-NPs reduces diabetes-induced retinal vascular leakage and retinal edema, and the effect lasts for at least 8 weeks after the injection, with a similar effect to that by oral administration daily.

Figure 5A:
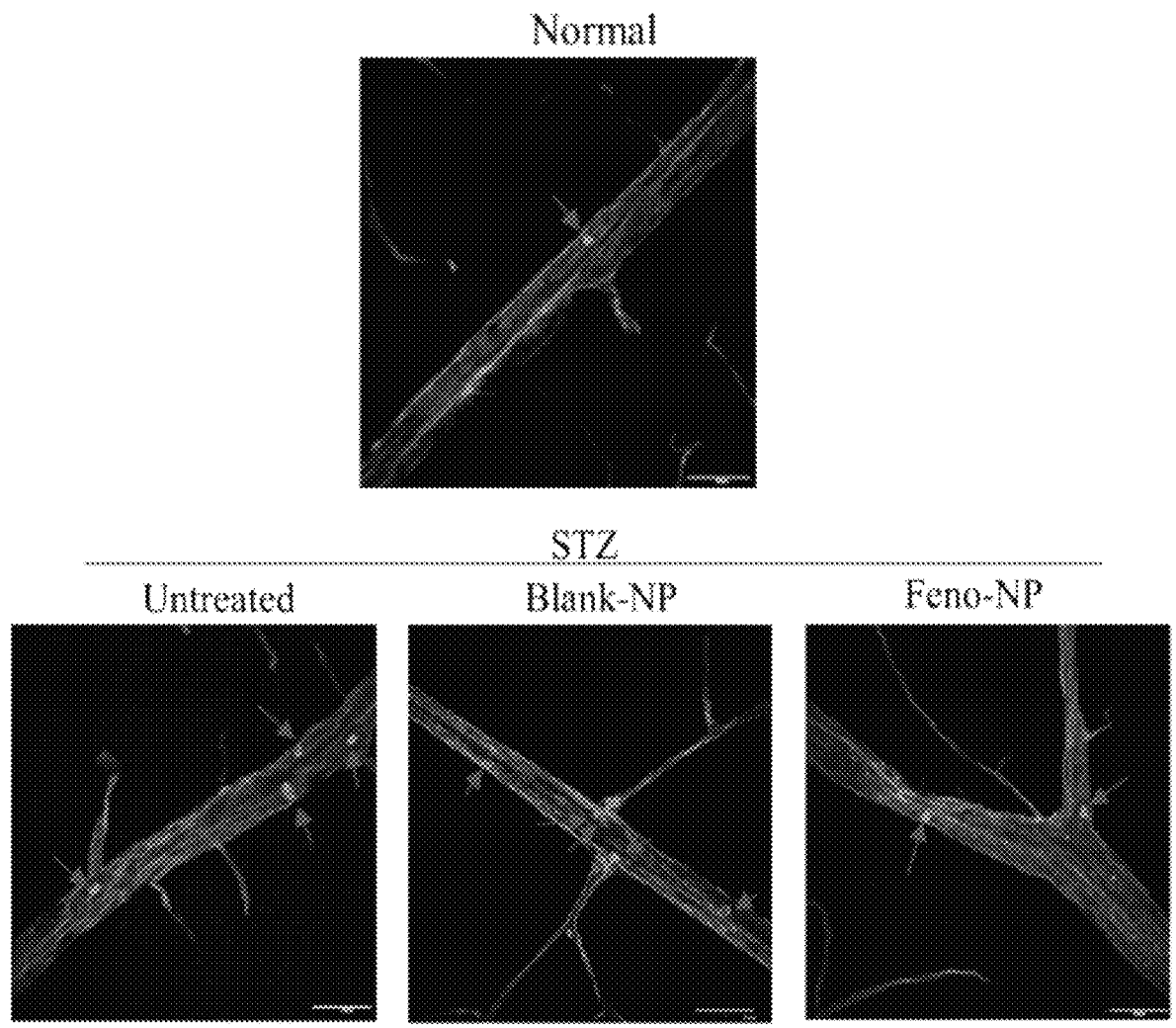
FIG. 5A shows the effect of Feno-NP$_{PLGA34kDa}$ on retinal vascular leukostasis in STZ-induced diabetic rats via representative images of retinal vascular leukostasis. Arrows indicate adherent leukocytes. Scale bar: 50 μm.
Figure 5B:
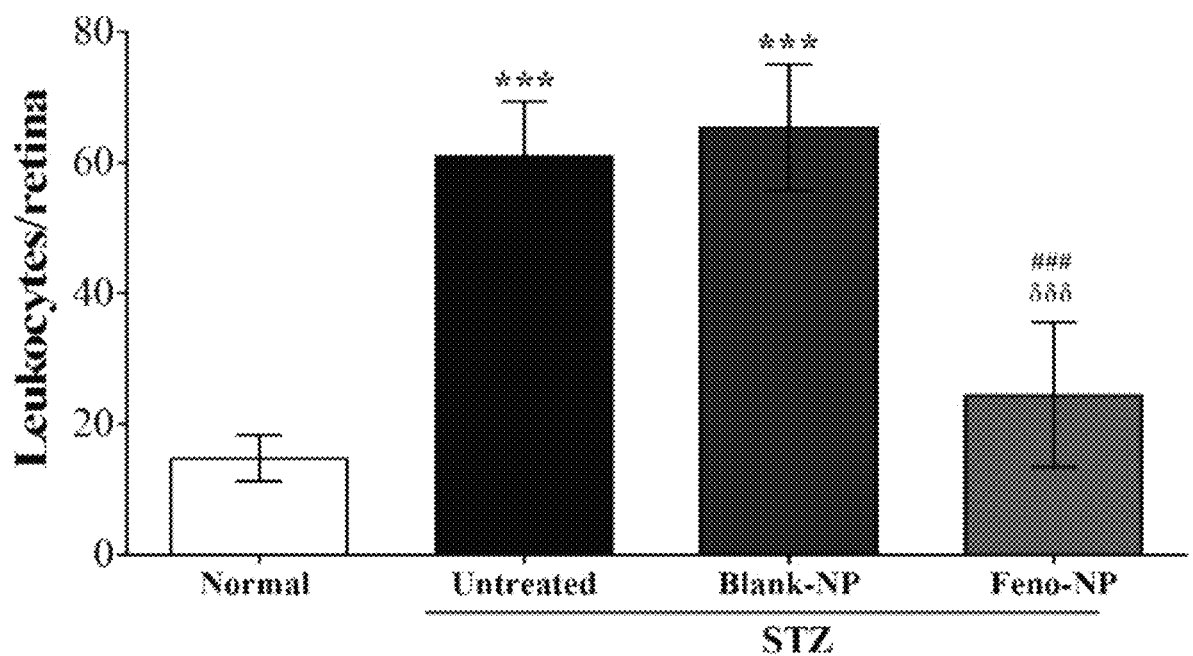
FIG. 5B shows quantification of leukocytes adherent to retinal vasculature 8 weeks after the Feno-NP treatment in FIG. 5A. Mean±SEM (n=7/group). Two-way ANOVA followed by Bonferroni post hoc test. *** P<0.001, versus normal rats. ###P<0.001, versus untreated diabetic rats. δδδ P<0.001, versus Blank-NP treated diabetic rats.

A Single IVT Injection of Feno-NP Reduces Leukostasis in STZ-Induced Diabetic Rats. Enhanced leukostasis, leukocyte adherence to the retinal vasculature, is another hallmark of DR. Retinal leukostasis is responsible for inducing retinal capillary nonperfusion, endothelium damage and vascular leakage. These results showed that numbers of adherent leukocytes were significantly increased in the retinal vasculature of diabetic rats, compared with that in nondiabetic control, and a single IVT injection of Feno-NPs, but not Blank-NPs, significantly decreased the number of adherent leukocytes 8 weeks after the injection, to a level in nondiabetic rats (FIG. 5A, B). These results indicate that Feno-NPs had an inhibitory effect on retinal vascular leukostasis, with the similar effect to that by oral administration daily.

Figure 6:
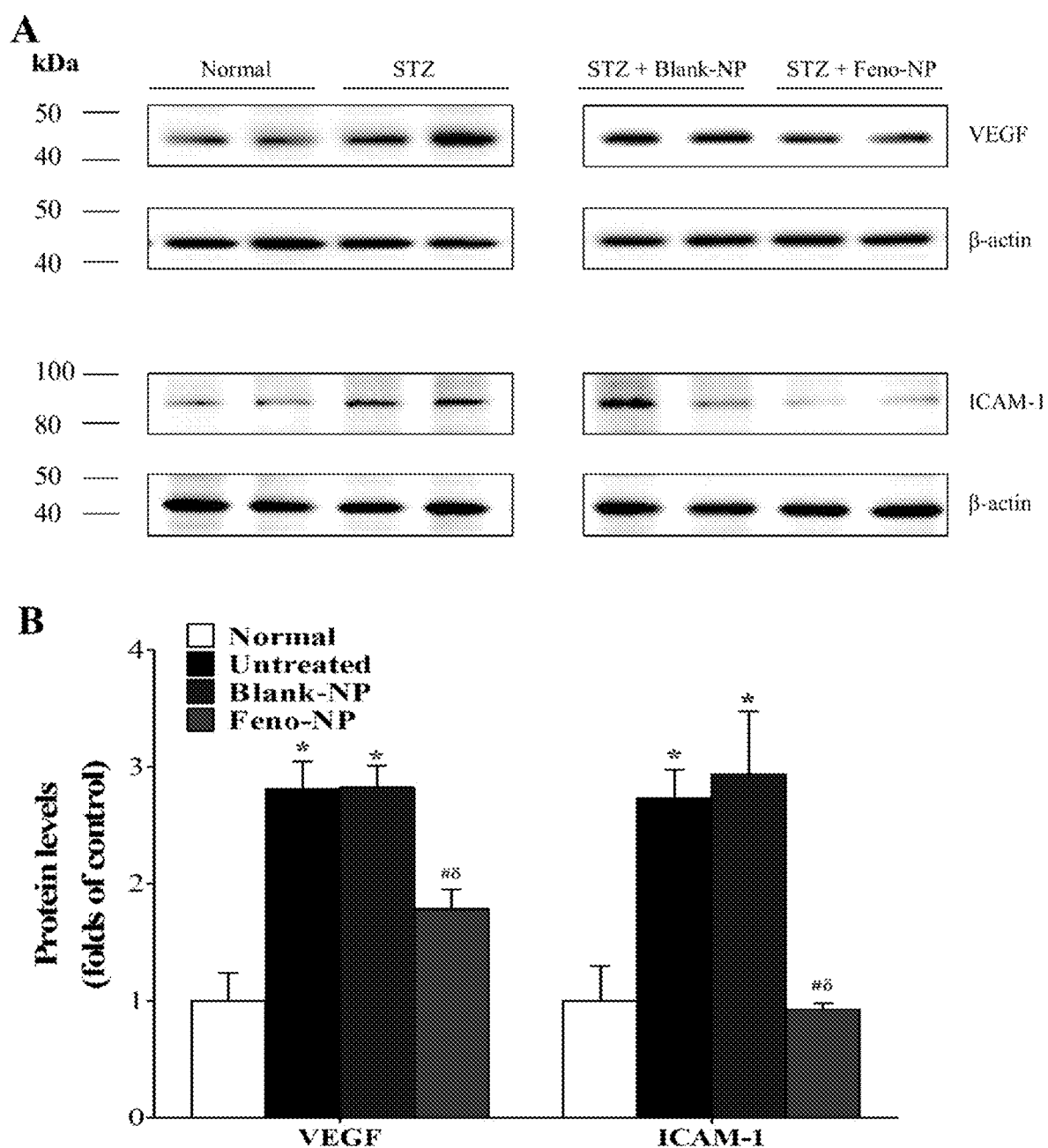
FIG. 6 shows the effect of Feno-NP$_{PLGA34kDa}$ on the overexpression of VEGF and ICAM-1 in the retinas of STZ-induced diabetic rat. The retinas were dissected for Western blot analysis 8 weeks after Feno-NP treatment. (A) Representative images of VEGF and ICAM-1 blots. (B) Quantification data of Western blot analysis. Mean±SEM (n=3/group). Two-way ANOVA followed by Bonferroni post hoc test. * P<0.05, versus normal rats. #P<0.05, versus untreated diabetic rats. δ P<0.05, versus Blank-NP treated diabetic rats.

Feno-NPs Attenuate the Overexpression of VEGF and ICAM-1 in the retina of Diabetic Rats. VEGF and ICAM-1 play important roles in retinal inflammation and vascular leakage in DR. As shown by Western blot analysis, both VEGF and ICAM-1 levels in the retina were elevated in diabetic rats compared with those of non-diabetic rats, while Feno-NPs, but not Blank-NPs, downregulated the overexpression of these two factors at 8 weeks after the injection (FIG. 6). These results indicate that Feno-NPs inhibit the overexpression of VEGF and ICAM-1 in the retinas of diabetic rats.

Figure 7A:
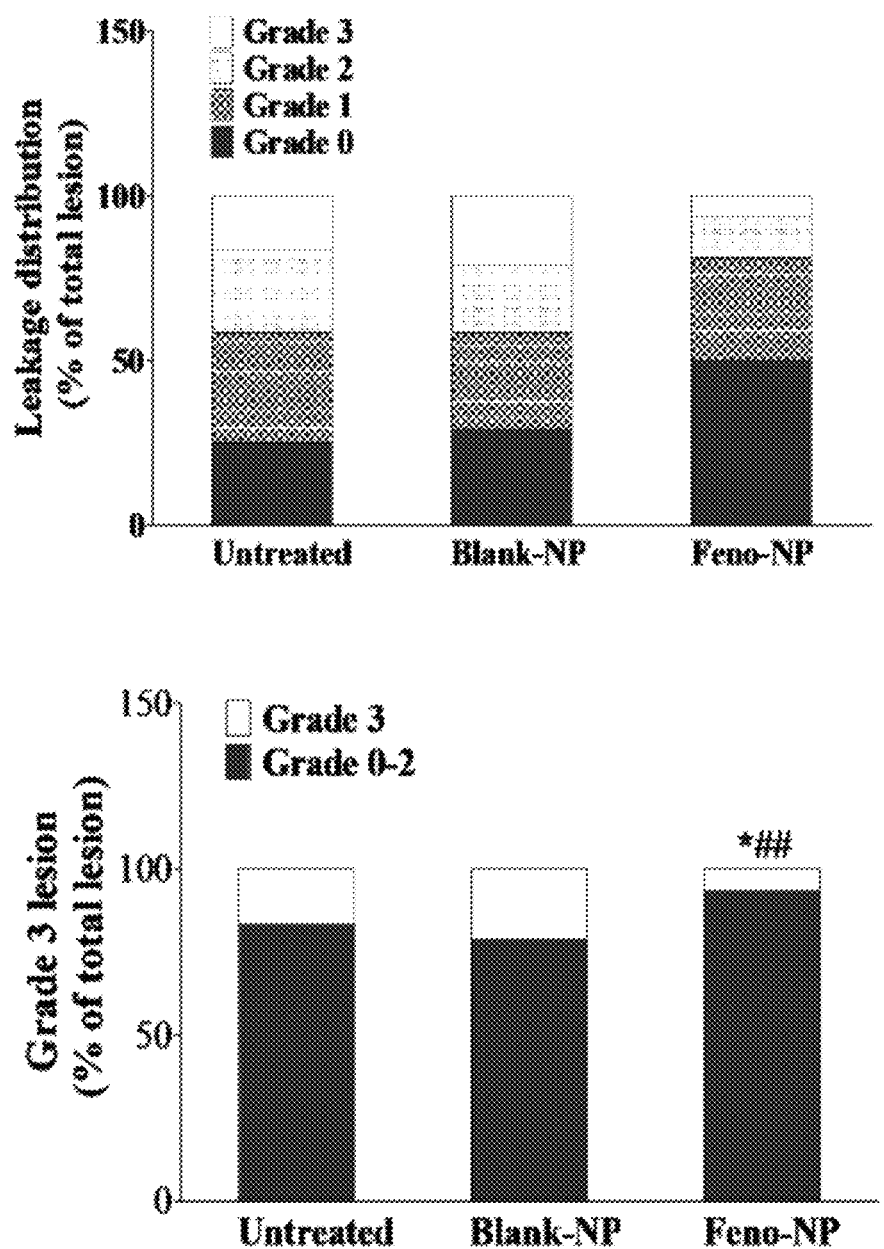
FIG. 7A shows the effect of Feno-NP$_{PLGA34kDa}$ on vascular leakage and the formation of choroidal neovascularization (CNV) in a laser-induced CNV rat model. Two weeks after Feno-NP treatment, vascular leakage was evaluated by fundus fluorescein angiography (FFA), and CNV evaluated by CNV area in choroidal flat mount. Distribution of lesion grades and the incidence of Grade 3 lesions with FFA (n=6-12). Data were percentages (%) (n=6-12) and analyzed by Chi-square test. * P<0.05, versus untreated CNV rats. ##P<0.01, versus Blank-NP treated CNV rats.
Figure 7B:
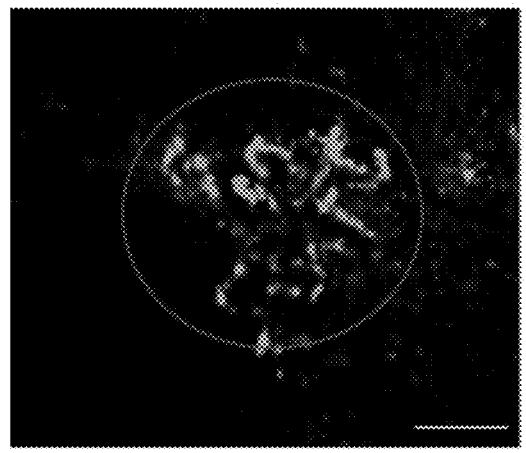
FIG. 7B shows representative images of choroidal flat mount in the rats of FIG. 7A. Red circles indicated CNV lesions. Scale bar: 50 μm.
Figure 7B:
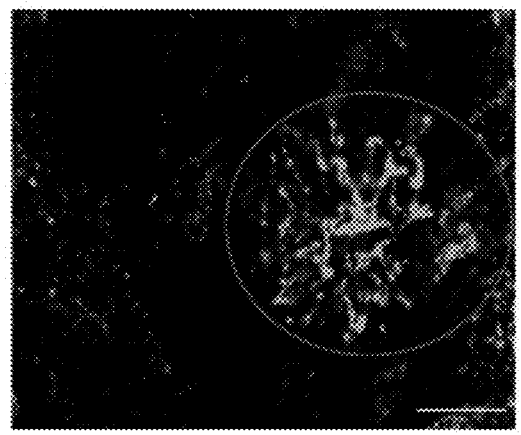
Figure 7B:
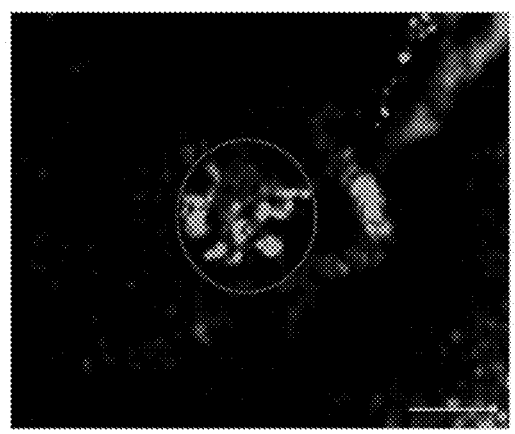
Figure 7C:
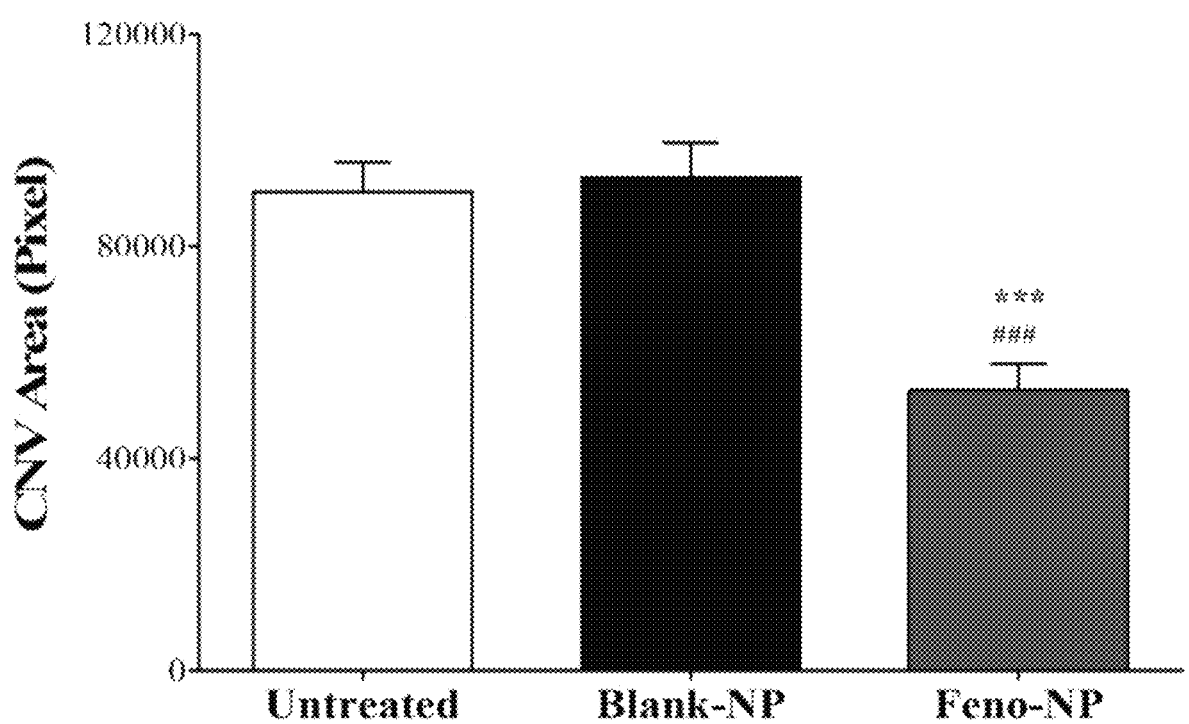
FIG. 7C shows quantification data of CNV area on choroidal flat mount in the rats of FIG. 7A. Mean±SEM (n=6-12). One-way ANOVA followed by Bonferroni post hoc test. *** P<0.001, versus untreated CNV rats. ###P<0.001, versus Blank-NP treated CNV rats.

A Single IVT Injection of Feno-NPs Reduces Vascular Leakage and Suppresses the Formation of CNV in Laser-Induced CNV Rats. We employed laser-induced CNV rats, a commonly used model of CNV with main characteristics of neovascular AMD. The distribution of CNV lesions with different degree of leakage was evaluated by FFA (FIG. 7A). It showed that the incidence of Grade 3 lesions, clinically significant CNV lesions, were significantly decreased in the Feno-NP group, but not in the Blank-NP group, compared with the untreated group. The incidence of Grade 3 is decreased about 70% in Feno-NP group, compared with the Blank-NP group, similar to the effect of fenofibric acid solution via i.p. injection daily. This result indicates that the Feno-NPs have an inhibitory effect on vascular leakage from laser-induced CNV in rats. For the evaluation of anti-angiogenic effects of Feno-NPs, the CNV area was measured in choroidal flat mounts following angiography with FITC-D. Feno-NPs, but not Blank-NPs, decreased CNV area compared with that in the group without treatment (FIG. 7B, C). The CNV area is decreased about 43% in Feno-NP group, compared with the Blank-NP group, similar to the effect of fenofibric acid solution via i.p. injection daily. These results demonstrate that Feno-NPs reduce the vascular leakage from CNV and suppresses the formation of CNV in laser-induced CNV rats, with the similar effect to that by systemic administration daily.

Figure 8A:
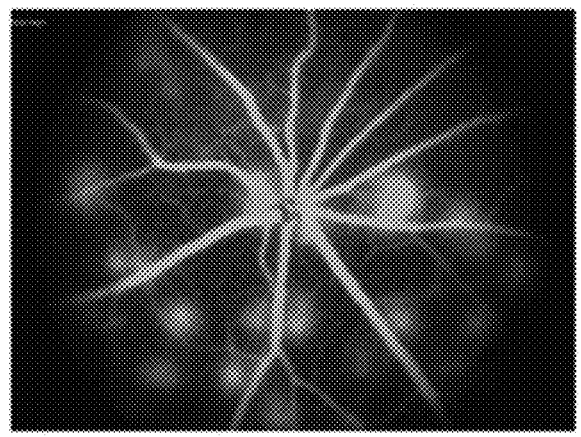
FIG. 8A shows in representative images of FFA the effect of Feno-NP$_{PLGA34kDa}$ on vascular leakage measured with FFA, and vascular permeability, formation of subretinal neovascularization (SRNV) and intraretinal neovascularization (IRNV) evaluated by neovascular tufts in flat-mounted choroid and retina in Vldlr$^{-/-}$ mice one month after Feno-NP treatment.
Figure 8A:
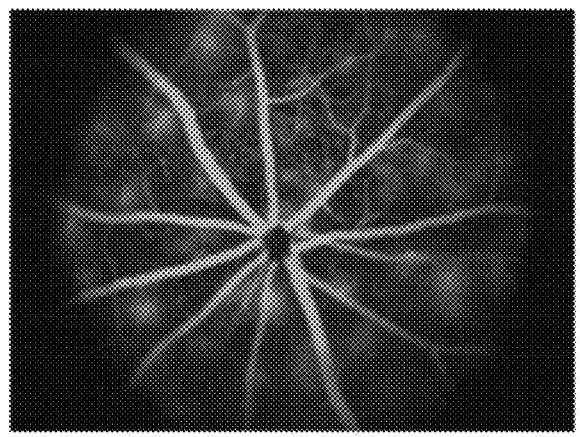
Figure 8A:
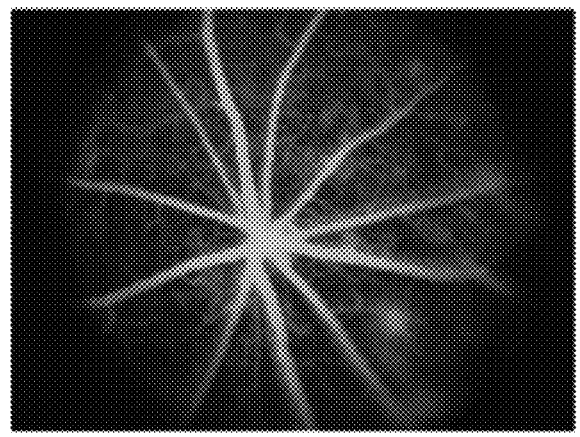
Figure 8B:
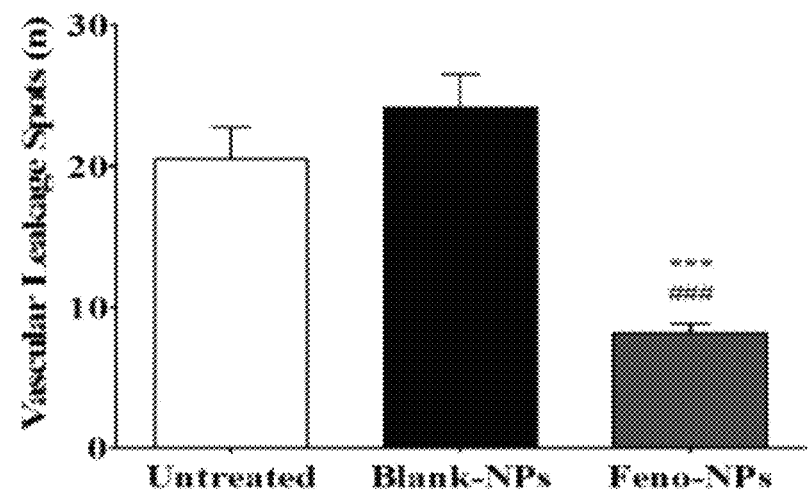
FIG. 8B shows numbers of leakage spots in FFA in the mice of FIG. 8A. Mean±SEM (n=8-16. One-way ANOVA followed by Bonferroni post hoc test. *** P<0.001, versus untreated Vldlr$^{-/-}$ mice. ###P<0.001, versus Blank-NP treated Vldlr$^{-/-}$ mice.
Figure 8C:
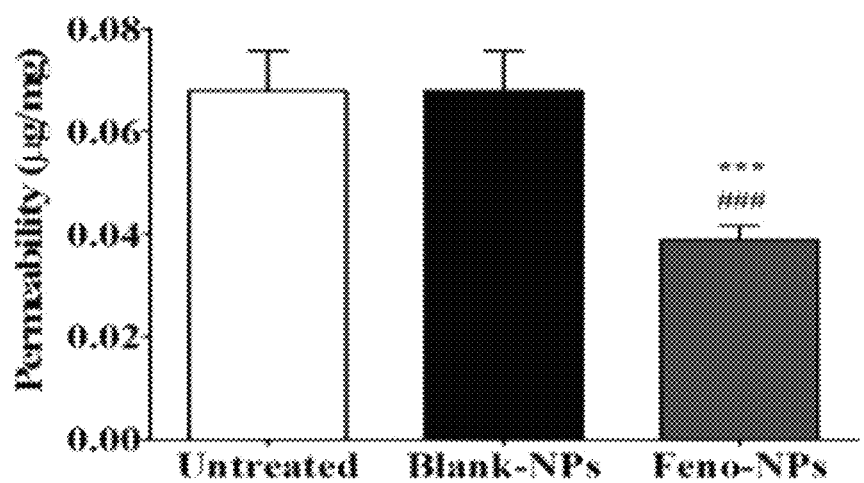
FIG. 8C shows quantification of retinal vascular permeability in the mice of FIG. 8A. Mean±SEM (n=8-16. One-way ANOVA followed by Bonferroni post hoc test. *** P<0.001, versus untreated Vldlr$^{-/-}$ mice. ###P<0.001, versus Blank-NP treated Vldlr$^{-/-}$ mice.
Figure 8D:
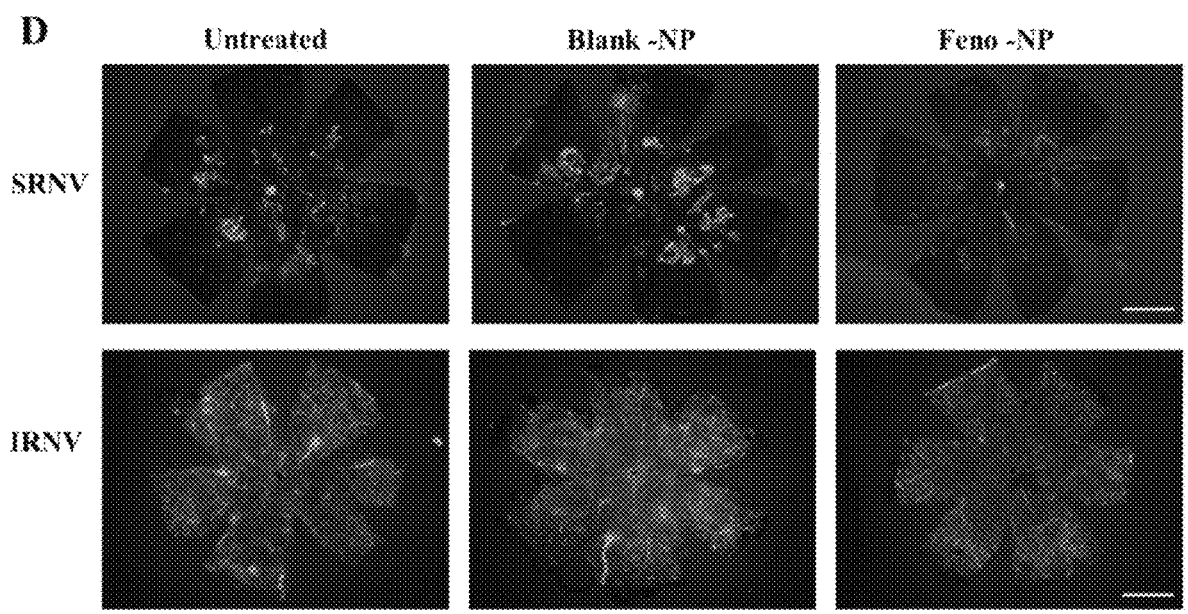
FIG. 8D shows representative images of SRNV and IRNV in FFA in the mice of FIG. 8A. Scale bar: 1,000 μm.
Figure 8E:
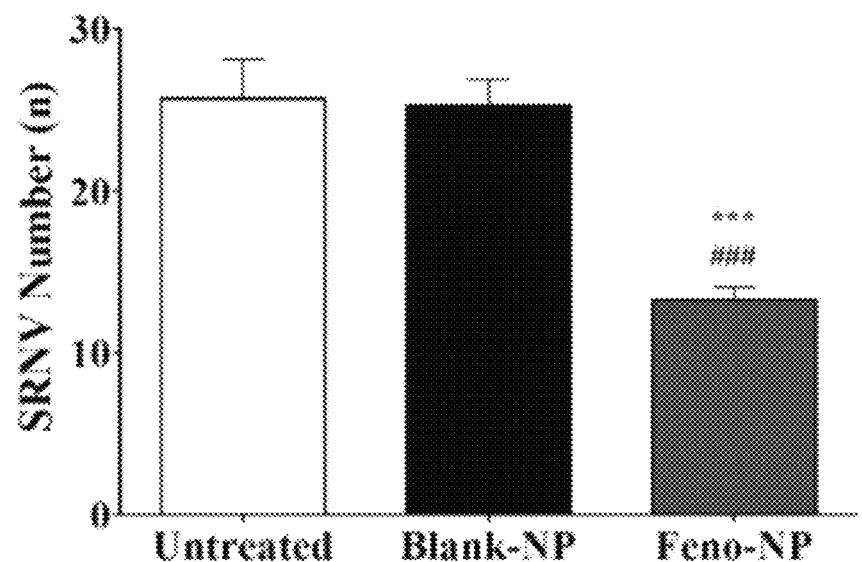
FIG. 8E shows quantification of SRNV (upper panel) and RNV (lower panel) in flat mounted choroid and retina in the mice of FIG. 8A. Mean±SEM (n=8-16. One-way ANOVA followed by Bonferroni post hoc test. *** P<0.001, versus untreated Vldlr$^{-/-}$ mice. ###P<0.001, versus Blank-NP treated Vldlr$^{-/-}$ mice.
Figure 8E:
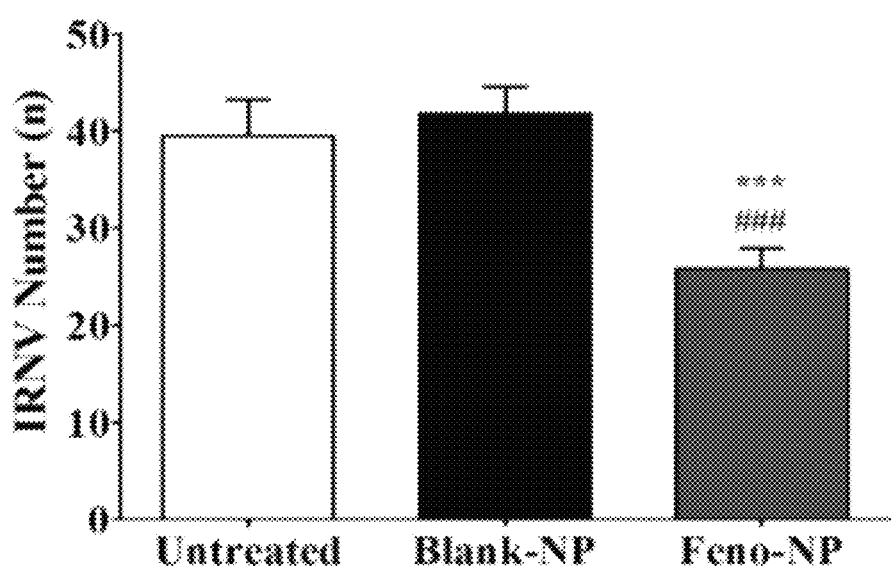

A Single IVT Injection of Feno-NPs Reduces Retinal Vascular Leakage and Suppresses the Formation of IRNV and SRNV in Vldlr$^{-/-}$ Mice. Vldlr$^{-/-}$ mice are a genetic model recapitulating some phenotypes of neovascular AMD such as subretinal NV and intraretinal NV. Feno-NPs, but not Blank-NPs, significantly reduced the retinal vascular permeability in Vldlr$^{-/-}$ mice, compared with Vldlr$^{-/-}$ mice without treatment, as shown by permeability assay using Evans blue as tracer (FIG. 8C). Consistently, FFA showed that Feno-NPs, but not Blank-NPs, significantly decreased the number of vascular leakage spots in the fundus of Vldlr$^{-/-}$ mice (FIG. 8A, B). These results indicate that Feno-NPs reduced retinal vascular leakage in Vldlr$^{-/-}$ mice. Moreover, we evaluated the effect of Feno-NPs on the formation of SRNV and IRNV in choroidal and retinal flat mounts following angiography with FITC-D. Numbers of both SRNV and IRNV were decreased significantly in the Feno-NP group, but not in the Blank-NP group, compared with Vldlr$^{-/-}$ mice without treatment (FIG. 8D, E), suggesting that Feno-NPs inhibit the formation of SRNV and IRNV in Vldlr$^{-/-}$ mice.

Figure 9A:
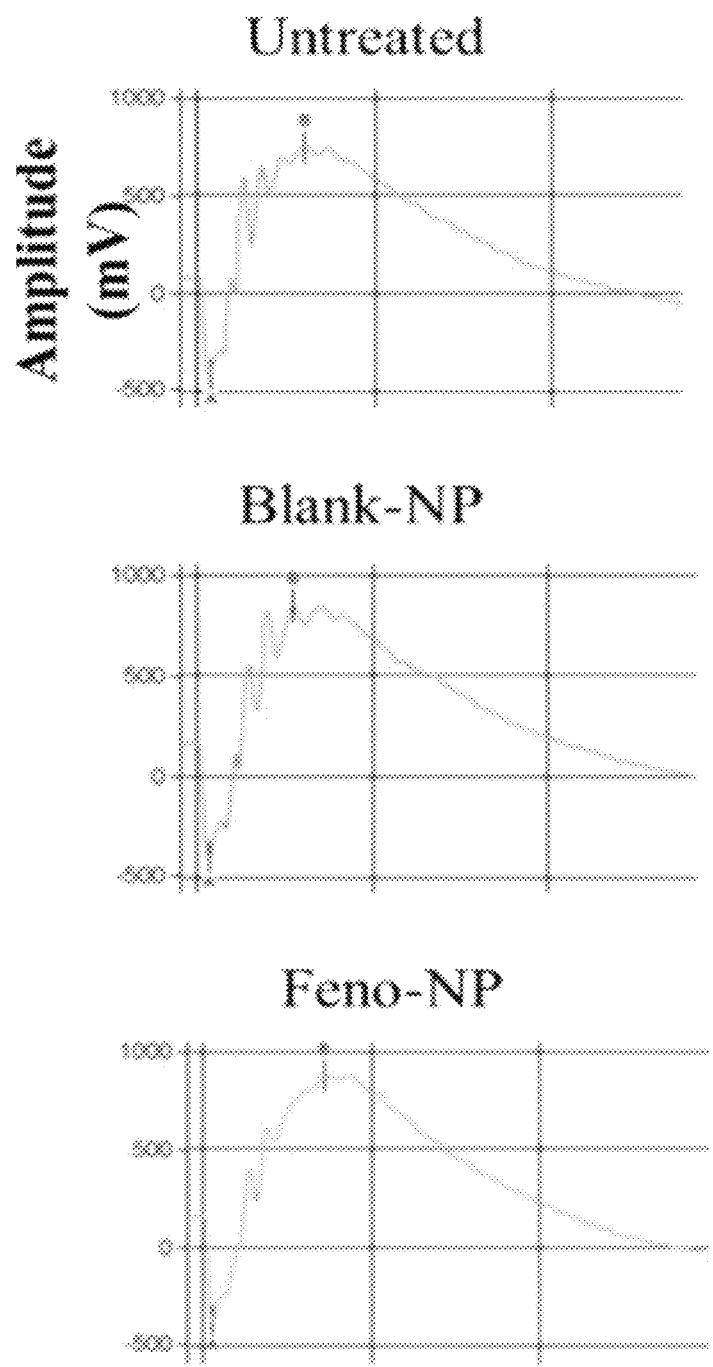
FIG. 9A shows representative ERG waveforms demonstrating that Feno-NP$_{PLGA34kDa}$ or Blank-NP has no detectable toxicities to retinal function measured with ERG and morphology with FP, OCT and FFA in normal rats.
Figure 9B:
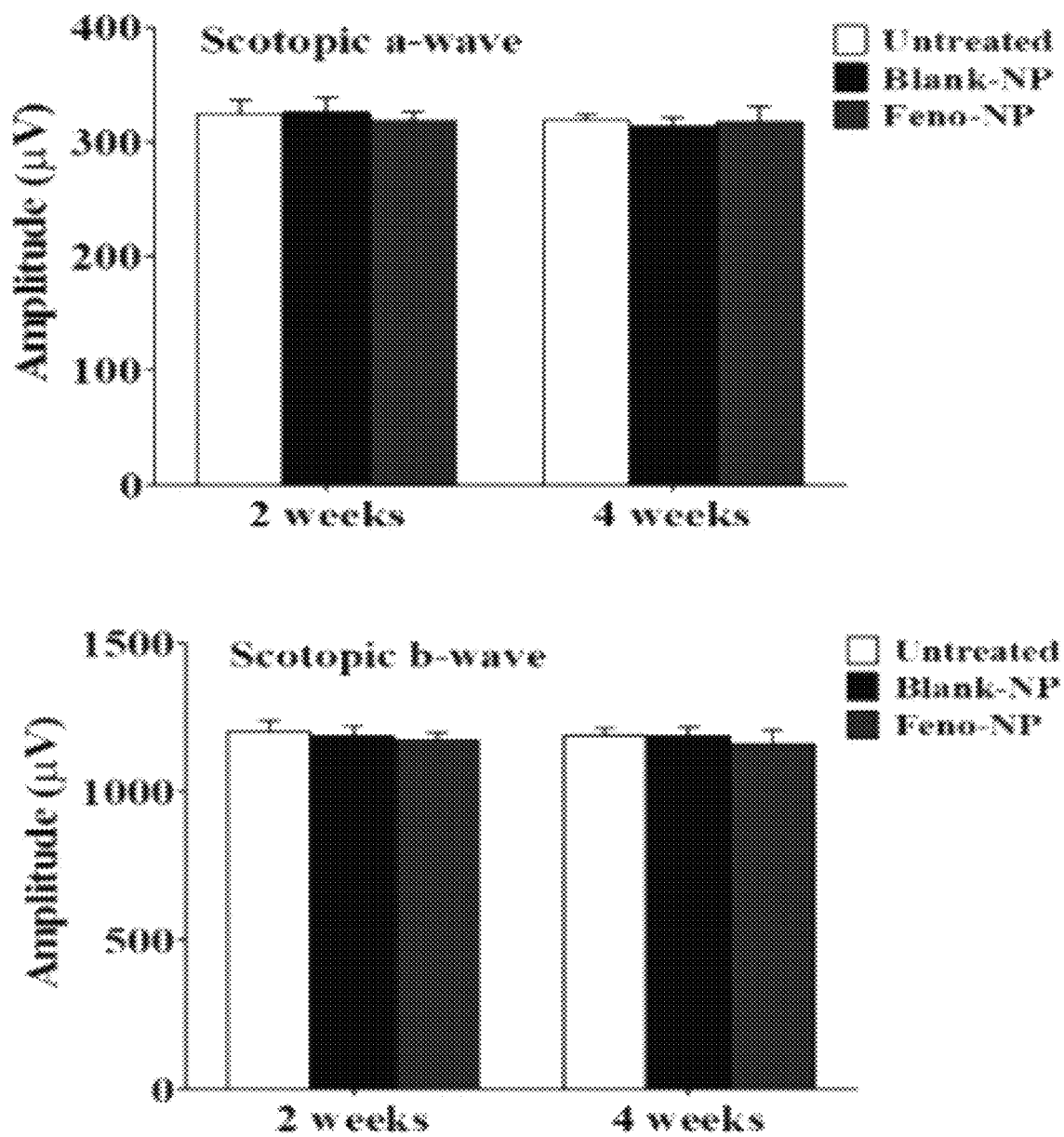
FIG. 9B shows quantifications of the ERG waveforms of the rats of FIG. 9A. Mean±SEM (n=8-16). One-way ANOVA followed by Bonferroni post hoc test. No statistically significant difference was found among untreated normal rats, Blank-NP treated normal rats and Feno-NP treated normal rats.
Figure 9C:
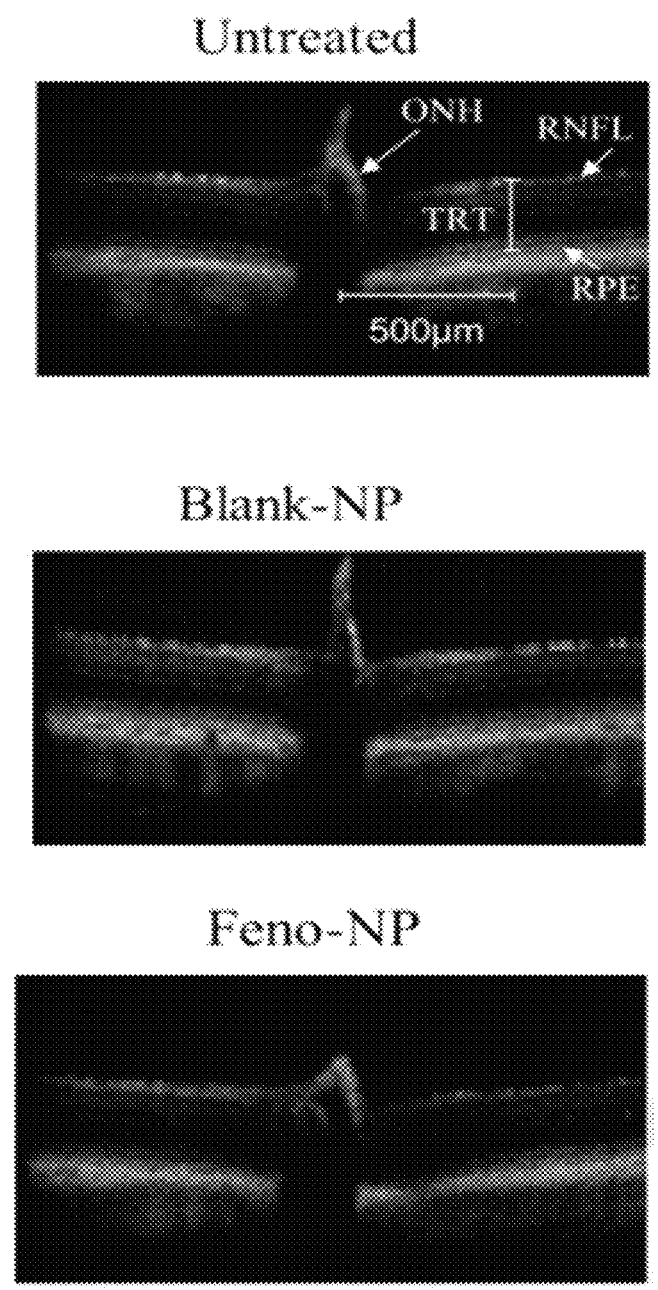
FIG. 9C shows representative images of OCT in the rats of FIG. 9A. TRT: total retinal thicknesses; RPE: retinal pigment epithelial layer; RNFL: retinal nerve fiber layer (RNFL); ONH: optic nerve head (ONH).
Figure 9D:
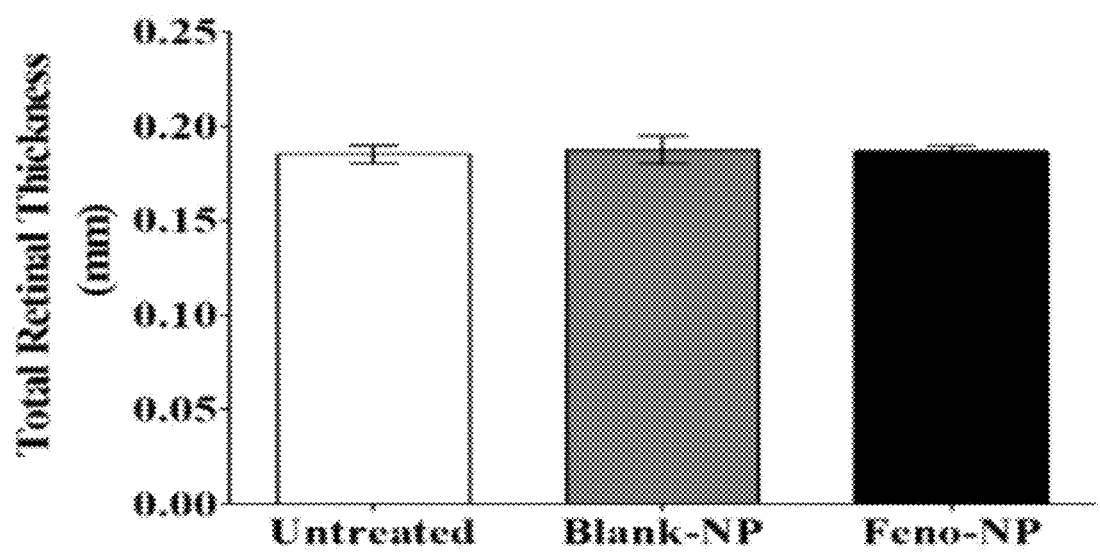
FIG. 9D shows quantification of total retinal thickness in OCT in the rats of FIG. 9A. Mean±SEM (n=8-16). One-way ANOVA followed by Bonferroni post hoc test. No statistically significant difference was found among untreated normal rats, Blank-NP treated normal rats and Feno-NP treated normal rats.
Figure 9E:
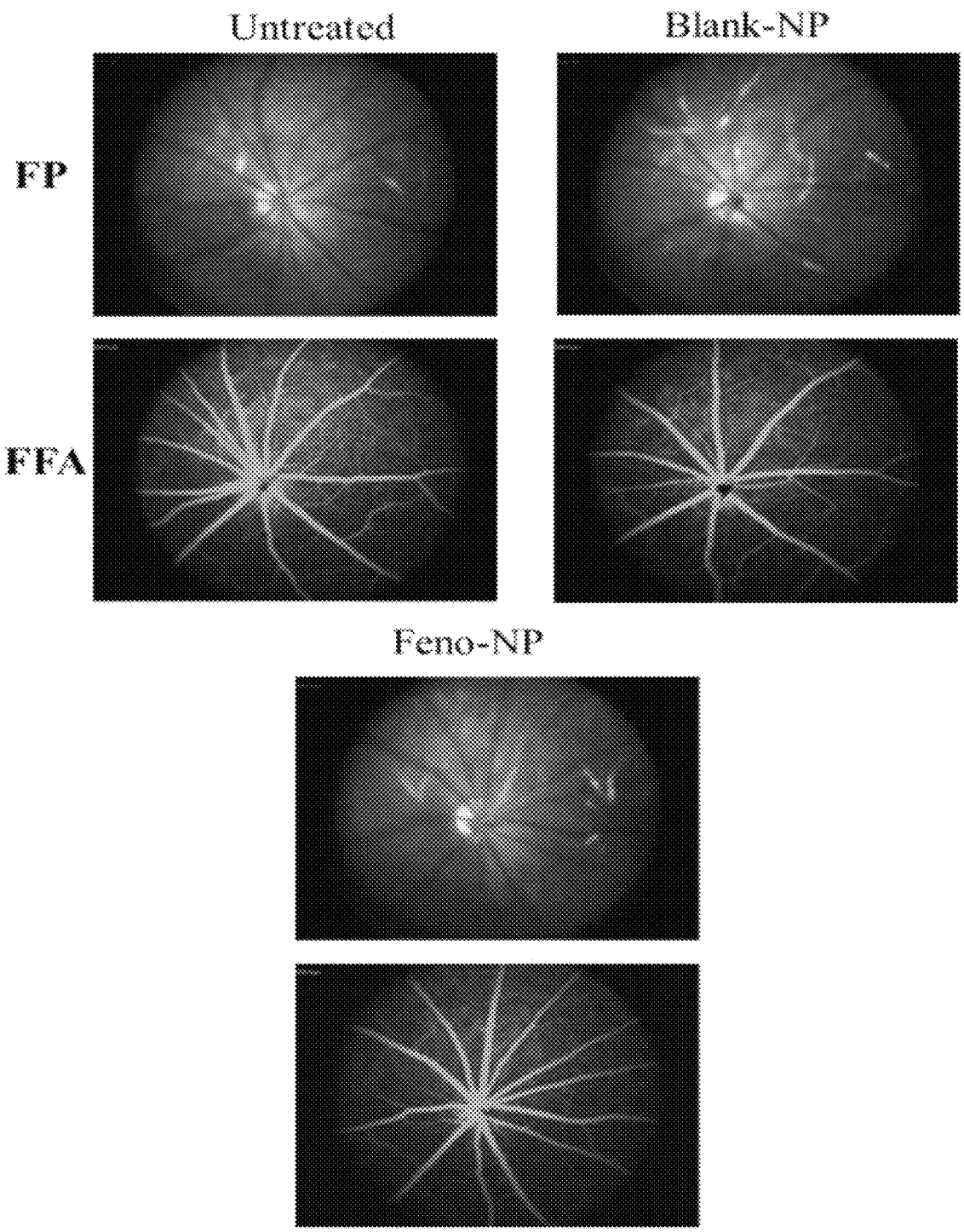
FIG. 9E shows representative images of FP and FFA in the rats of FIG. 9A.

Intraocular Injection of Feno-NPs Has no Detectable Toxicities to the Structure and Function of the Retina. As shown by ERG (FIG. 9A, B), there was no significant difference in amplitudes of both scotopic a- or b-waves among untreated normal rats and those treated with Feno-NPs and Blank-NPs at both 2 weeks and 4 weeks following NP injection, suggesting that neither Feno-NPs nor Blank-NPs have toxicity to retinal function in normal rats. Structurally, retina appearance was normal and no retinal detachment, hemorrhage, or evidence of fibrosis was observed in the groups treated with Feno-NPs or Blank-NPs at 4 weeks after injection, and Blank-NP groups, as shown by FP (FIG. 9E). In FFA, the retinal vasculature in the eyes treated with NP injection was similar to those without NP injection, with no changes in vascular leakage (FIG. 9E). Similarly, no difference was observed in total retinal thickness as shown by OCT among normal rats injected with Feno-NPs, Blank-NPs and without NP injection (FIG. 8C, D). Altogether, no severe ocular toxicity was observed during the experimental period after the IVT injection of NPs in rats.

Discussion

PPARα is a nuclear transcription factor for diverse target genes, and regulates many biological processes including vascular function, oxidative stress, and inflammation. Previous work demonstrated that downregulated PPARα plays a pathological role in diabetic microvascular complications in animal models. We also showed that Pparα$^{-/-}$ mice developed more severe laser-induced CNV, compared with wild type mice, indicating that downregulated PPARα promotes the development of CNV. In addition, Pparα$^{-/-}$ mice showed increased ischemia-induced retinal cell death in the OR model in comparison to wild type mice, suggesting the downregulated PPARα plays a pathogenic role in retinal degenerative diseases. PPARα activation has potent anti-inflammatory activities. The activation of NLRP3 inflammasome plays a pivotal role in the development and progression of inflammatory diseases including ocular diseases such as DR, AMD, glaucoma and dry eye. Fenofibrate, a PPARα agonist, improves the endothelial precursor cell function and protects retinas from neuroinflammation via downregulating the activity of NLRP3. It was also demonstrated that fenofibrate has potent therapeutic effects on diabetic microvascular complications in patients, and displays anti-inflammatory and anti-angiogenic activity on DR and neovascular AMD in animal models, through activation of PPARα.

Two large longitudinal clinical trials have independently reported a surprising finding that oral administration of fenofibrate has a robust beneficial effect in DR in Type 2 diabetic patients, independent of its effect on dyslipidemia. A previous study demonstrated that oral administration of fenofibrate reduced retinal vascular leakage in the STZ-induced diabetes rat model and a genetic diabetic mouse model. Further, IVT injection of fenofibrate also reduced the vascular leakage in the STZ-induced diabetes rat model and OIR rat model [22]. Recently, it was shown that i.p. injection of fenofibric acid, the active form of fenofibrate, also has therapeutic effects on neovascular AMD as shown by reduced vascular leakage and formation of CNV or RNV in laser-induced CNV rats and Vldlr$^{-/-}$ mice.

Fenofibrate exhibits low oral bioavailability because of its high lipophilicity. In order to enhance the drug solubility and increase the oral bioavailability, attempts were made to formulate fenofibrate nanocrystals, and fenofibrate-encapsulated solid lipid NP. Polyvinylpyrrolidone, hydroxypropyl-β-cyclodextrin and gelatin were applied to prepare fenofibrate-encapsulated polymeric NP as potential oral formulations to enhance the bioavailability of fenofibrate by increasing the drug dissolution. Fenofibrate-loaded PLGA microparticles were prepared for treating ischemic stroke, and the drug release only lasted for 7 days. None of these formulations would be suitable for IVT administration for treating DR and AMD to provide sustained efficacy up to a few months. Fenofibrate could also be potentially formulated as a drug crystal suspension for IVT injection, but drug suspension typically exhibit uncontrollable drug dissolution profiles. Here, we demonstrated that a biodegradable NP platform with high drug loading and sustained release of fenofibrate effectively alleviated choroidal and retinal NV in rats through a single IVT injection, which avoided repeated injections.

The Feno-NP (and other M/NP) formulations can be further altered to increase drug (active agent) loading and drug release profiles by changing polymer composition and process parameters. When PLGA polymers with the same terminal carboxyl groups and LA:GA ratio, lower molecular weight PLGA (e.g. PLGA 5 kDa) are less hydrophobic than higher molecular weight PLGA (e.g. PLGA 54 kDa). Thus, more hydrophobic PLGA 54 kDa could achieve higher drug loading of 7.9% than the less hydrophobic PLGA5kDa (only 1.1%). Sustained release of fenofibrate from Feno-NP is likely a result of both the gradual degradation of PLGA and diffusion of fenofibrate through the PLGA matrix. The degradation of PLGA is influenced by the degree of polymer crystallinity, which is affected by the LA:GA ratio, and higher content of PGA leads to quicker degradation. An exception is that PLGA (50:50) is amorphous with fast hydration and exhibits the fastest degradation. PLGA with acidic terminal groups demonstrated faster degradation than ester-terminated PLGA. PLGA (50:50) with carboxyl terminal groups can degrade fast, and the nano-sized NP will facilitate water penetration into NP matrix allowing quick hydrolysis. Therefore, we observed a steady drug release profile without a significant lag phase following the initial rapid drug release, unlike typical PLA/PLGA microspheres. Lower molecular weight PLGA 5 kDa NP typically degrades quickly and exhibits a fast drug release profile (all drug released within 1 week in vitro), and the higher molecular weight PLGA 54 kDa NP degrades much slower with sustained drug release lasting for more than 2 months in vitro. We can further increase the drug loading and prolong the drug release by increasing the particle size or using more hydrophobic and less degradable PLGA/PLA.

Feno-NPs were manufactured with components that are classified as GRAS materials by the FDA for various uses and have a long history of use in pharmaceutical products, including ophthalmic formulations. PLGA is known to form natural metabolites (lactic and glycolic acids) and is eliminated from the body, offering the advantage of safety. However, cytotoxicity is still a potential concern in nanoparticle-mediated drug delivery. In the present work the potential toxicity of Feno-NPs and Blank-NPs in the retina in normal rats was investigated. Analyses of the ERG response, retinal morphology and retinal vasculature indicated that Feno-NP had no detectable side effects on retinal structure and function. The present results indicate that Feno-NP are safe to the normal retina for intraocular administration at the dose used. We noticed an increased trend of permeability in diabetic rats treated with blank-NP, but this increase had no statistical significance. The IVT injection procedure is a known insult to the retina which may cause retinal inflammatory responses, leading to high permeability.

Particles having diameters up to 50 μm can be injected with 27G needles. The 250 nm size of the Feno-NPs allow IVT injection in both animals and patients through fine gauge needles (e.g. 30G). The emulsification method used to prepare Feno-NP is a scalable procedure, facilitating large-scale manufacturing of the NPs. Other solvents (e.g. ethyl acetate and benzyl alcohol) with improved safety profiles can be used to replace the DCM at the emulsification procedure to manufacture Feno-NPs. Clinic trials demonstrated that the IVT dexamethasone PLGA implant, Ozurdex®, can sustain the release of dexamethasone in the vitreous cavity to provide therapeutic effects up to 6 months in patients with diabetic macular edema, and showed no obvious retinal toxicity caused by PLGA itself even after repeated applications A previous study showed that one single IVT injection of plasminogen kringle 5 loaded PLGA NP (K5-NP) decreased CNV area in a laser-induced CNV rat model for up to 2 weeks, as well as reduced retinal NV in the ischemia-induced retinal NV rat model for at least 4 weeks.

Fenofibrate, and other active agents noted herein, has potential anti-inflammatory activities, which, may contribute to its protective effects against microvascular impairment and neuronal cell death in many diseases. The results disclosed herein demonstrated that Feno-NPs attributed to its anti-inflammatory effects by reducing the retinal leukostasis, downregulating the overexpression of VEGF and ICAM-1, and attenuating retinal vascular leakage in STZ-induced diabetic rats, consistent with previous results using free fenofibrate in the OIR rat model and STZ-induced diabetic rat model. In addition, the present work showed a novel finding that Feno-NPs rescued retinal dysfunction in STZ-induced diabetic rats. These results indicate that Feno-NPs, similar to free fenofibrate, have beneficial effects on DR. Free fenofibrate after IVT dosing, the active drug levels will decline quickly and disappears in less than 1 week. However, compared with fenofibrate free drug, the Feno-NPs of the present disclosure have sustained effects. In one non-limiting embodiment, the effects lasted for at least 8 weeks after a single injection (30 μg fenofibrate for rats and 9 μg for mice), which provided continuous effective fenofibric acid level in the eye resulting in the need of greatly reduced injection frequency. In order to achieve similar efficacy in the same animal models, a frequent and high systemic dosing for a long period would be required through either daily i.p. injection at~25 μg/g/day for 2 weeks (5 mg/day per rat and 0.5 mg/day per mouse), or daily oral administration at~120 μg/g/day for 7 weeks (24 mg/day per rat). IVT injection of Feno-NP significantly reduced the total dose by~2000 times and~40,000 times in comparison to the i.p. and oral route, respectively. Also, the overall effect of Feno-NPs in the present work showed a similar efficacy in comparison to fenofibrate administrated systemically in diabetic rats and laser-induced CNV rats. Therefore, the local IVT delivery of Feno-NPs has advantages over a fenofibrate solution, not only by lowering the drug dose of fenofibrate, but also by reducing the frequency of more invasive IVT injections, subsequently decreasing the incidence of high-dose fenofibrate induced nephrotoxicity and the risks associated with frequent IVT injections. As noted above, the Feno-NP formulations can be further modified to achieve increased drug release duration≥6 months, e.g., 6-12 months. Thus, in certain embodiments, using the present technology, IVT dosing of patients with AMD and DR can be reduced to once to twice per year.

Diabetic stress results in the over-production of inflammatory factors including VEGF and ICAM-1 in the retina. ICAM-1 mediates leukostasis, and VEGF increases retinal leukostasis and vascular permeability. Increased retinal vascular leukostasis leads to retinal capillary closure, causing nonperfusion of vessels, damages the retinal endothelium and promotes vascular leakage, leading to macular edema and NV which is responsible for vision loss. Previous work demonstrated that fenofibrate exerts its beneficial effects on DR via activation of PPARα. Therefore, without wishing to be bound by theory, it is possible that fenofibric acid activates PPARα, resulting in the downregulation of VEGF and ICAM-1 expression, which in turn inhibits retinal leukostasis, decreases retinal microvasculature impairment, reduces vascular leakage, and ultimately protects retinal dysfunction in DR. Although numerous studies have shown retinal vascular leakage or increased vascular permeability in STZ-diabetic rats, actual retinal edema has not been demonstrated in this model. Using OCT, the present work demonstrated the increase of retinal thickness in STZ-diabetic rats, suggesting retinal edema is present in this model. Feno-NP injection significantly reduced retinal thickness in diabetic rats to levels similar to that in non-diabetic rats. This observation is consistent with reduced retinal vascular leakage and reduced levels of ICAM-1 and VEGF in diabetic retinas. These results indicate that Feno-NPs alleviate diabetic retinal edema. The beneficial effects of Feno-NPs in neovascular AMD were also demonstrated by showing that a single IVT injection of the Feno-NPs reduced vascular leakage and attenuated the formation of CNV in both the laser-induced CNV rat model, a commonly used CNV model, and Vldlr$^{-/-}$ mice, a genetic model of intra-retinal and sub-retinal NV. Feno-NPs thus offer an innovative strategy for delivery of fenofibrate by IVT injection, providing a therapeutic approach for macular edema and NV in DR and AMD.

Degradation rates of the polymer used to encapsulate the fenofibrate and accompanying release profiles of drugs can be controlled by the polymer's physicochemical properties, such as molecular weight, hydrophilicity, and the ratio of monomers in the case of copolymers. The drug release from PLGA M/NPs can be prolonged by increasing the polymer molecular weight, the lactide:glycolide ratio, or the particle size.

In conclusion, Feno-NPs have been successfully formulated using the emulsification method, and these conferred sustained therapeutic effects in both DR and neovascular AMD. Feno-NPs showed desired physiochemical characteristics and sustained release profiles. A single IVT injection of the Feno-NPs displayed therapeutic results for the treatment of DR and neovascular AMD with prolonged drug release and thus reduced injection frequency. In addition, the Feno-NPs are safe for administration to the retina.

Example 2

In earlier work, fenofibrate was encapsulated into PLGA NPs that provided more than 3 months efficacy in DR and neovascular AMD after a single IVT injection. Compared with such NPs, microparticles (MPs) possess larger particle sizes that contribute to a drug release sustained for a longer duration. Considering the potential efficacy of PPARα agonist on DR and neovascular AMD, we established a PPARα agonist-loaded microparticle platform that can provide long-lasting PPARα agonist release in the posterior segment of the eye, including for example, fenofibrate MPs and pemafibrate MPs.

Pemafibrate is a selective PPARα modulator with higher potency and selectivity for PPARα activation than fenofibrate. In cell-based transactivation study, pemafibrate showed high activity in PPARα activation (EC50=0.08 nM) and an extremely subtype selectivity (>5000, >11,000-fold for PPARγ, PPARδ, respectively), making it 2500 times more potent than fenofibric acid (EC50=30 µM for PPARα), the active form of fenofibrate. In this example, we established a PPARα agonist MP platform that can provide long-lasting pemafibrate release in the posterior segment of the eye.

Methods
Preparation of Microparticles
Pemafibrate-loaded microparticles (Pema-MPs). Pema-MPs were prepared using an emulsification method. In brief, 20 mg pemafibrate and 100 mg PLA$_{54k}$ or PLA$_{76k}$ were dissolved in 1 ml DCM. The mixture was added into 60 ml 1% PVA under homogenization at 5000 rpm using a Silverson homogenizer for 2 min. The formed emulsion was poured into an additional 100 ml 0.3% PVA solution under stirring at 700 rpm. An hour later, the suspension was putted in a vacuum chamber to further remove DCM for another 3 h. The Pema-MPs were filtered using 40 µm strainer, washed with DI water for three times, and collected by centrifugation under 500 g for 10 min.

Fenofibrate-loaded microparticles (Feno-MPs). Feno-MPs were prepared using an emulsification method. In brief, 20 mg fenofibrate and 100 mg PLGA$_{54k}$ (or PLGA$_{45k}$-PEG$_{5k}$, or the blend of PLGA$_{54k}$ and PLGA$_{45k}$-PEG$_{5k}$) were dissolved in 1 mL dichloromethane (DCM). The mixture was poured into 60 mL of 1% PVA solution under homogenization at 5000 rpm using a Silverson homogenizer. The formed emulsion was added to an extra 100 mL 0.3% PVA solution under magnetic stirring at 700 rpm for 1 hour. The suspension was placed in a vacuum chamber for another 3 hours under stirring to further remove DCM. The Feno-MPs were filtered with 40 µm strainer, washed with DI water and collected by centrifugation at 500×g for 10 minutes.

Particle characterization. The particle sizes of the MPs were measured using Multisizer 4 Coulter Counter (Beckman Coulter Inc., Brea, Calif.). Morphology of microparticle was obtained using a scanning electron microscope (SEM).

Drug loading and in vitro drug release. A predetermined amount of lyophilized microparticle was fully dissolved in acetonitrile, and the fenofibrate/pemafibrate concentration in the solution was quantified by HPLC after filtering through 0.22 µm filter. Isocratic separation was conducted on Shimadzu LC-2030C 3D plus system equipped with Agilent C18 column (250×4.6 mm). The mobile phases consist of acetonitrile/water (80/20 for fenofibrate and 75/25 for pemafibrate) containing 0.1% trifluoroacetic acid (flow rate=1 mL/min). Column effluent was monitored by UV detection at 285 nm for fenofibrate and 280 nm for pemafibrate. Fenofibrate/pemafibrate concentration was calculated using an established standard curve. The drug loading (DL) and encapsulation efficiency (EE) were calculated as follows:

$$DL\ (\%) = \frac{\text{amount of fibrate in particles}}{\text{weight of particles}}$$

$$EE\ (\%) = \frac{\text{actual drug loading}}{\text{theoretical drug loading}}$$

In vitro drug release profile of fenofibrate and pemafibrate was measured by placing 400 µl MP suspension (about 1 mg fenofibrate/pemafibrate) in dialysis tubing cellulose membrane (MW cutoff: 10 kDa, Sigma Aldrich, St. Louis, Mo.). The sealed dialysis membrane was placed in 50 ml conical tubes containing 13 ml PBS (0.2% tween-80 PBS, pH 7.4). The whole system was incubated at 37° C. on a platform shaker (140 rpm). The entire release medium was collected at predetermined time point and replaced with another 13 ml PBS (0.2% tween-80 PBS) solution. Fenofibrate/pemafibrate amount in the release medium was quantified using HPLC as described above.

Figure 10:
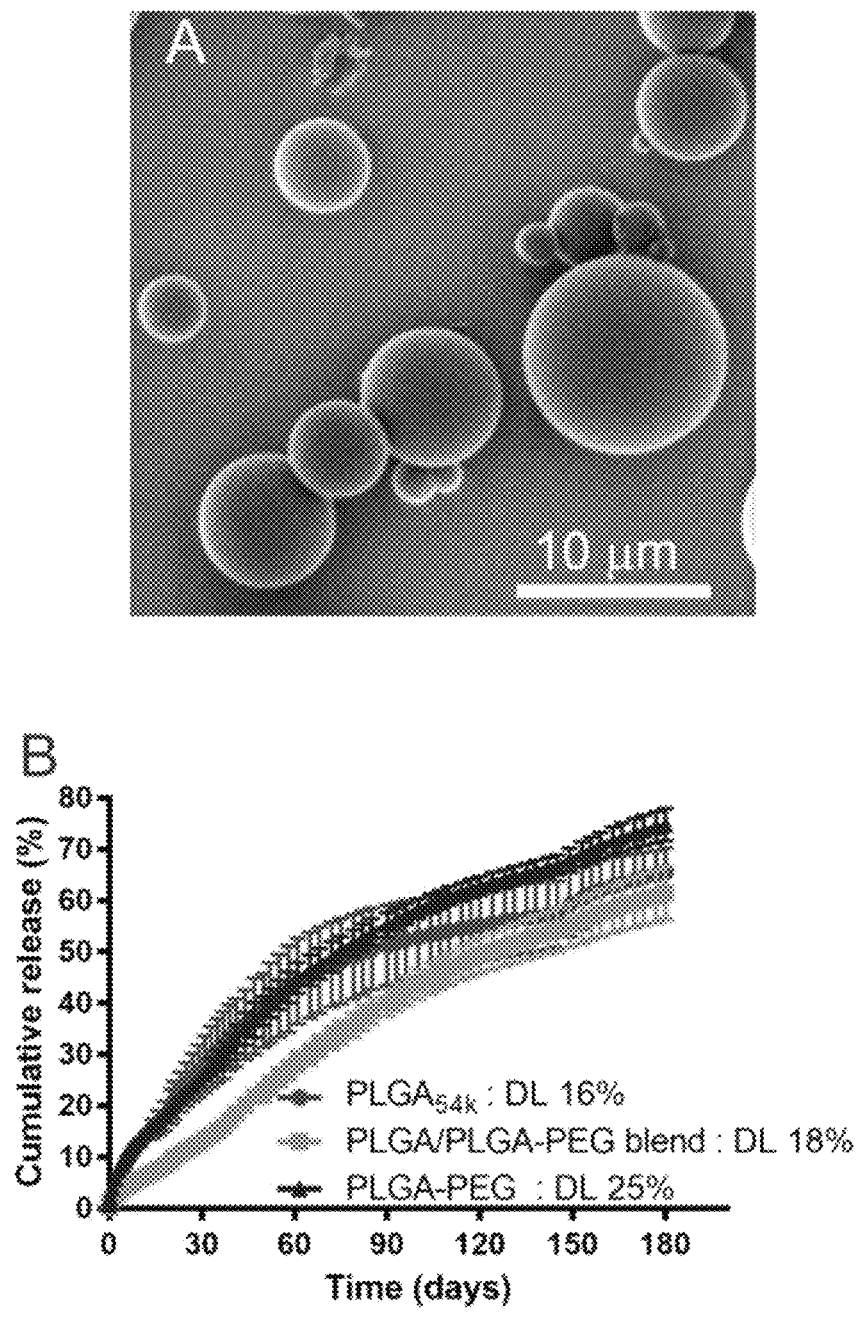
FIG. 10 shows in (A) a representative scanning electron microscopy (SEM) image of Fenofibrate-loaded PLGA$_{54k}$ microparticles (Feno-MP) with average particle size of 3.8±1.8 μm, and in (B) that Feno-MP exhibited high drug loading (DL) of~20% wt/wt, and provided up to at least 6 months sustained release of fenofibrate in vitro. n=3 repeats.

Results
Physiochemical characterization of Feno-MPs. Fenofibrate was successfully encapsulated into microparticles. Since higher molecular weight PLGA generated higher drug loading. We only used PLGA$_{54k}$ and PLGA (50:50)$_{45k}$-PEG$_{5k}$ in the preparation of Feno-MPs. Physiochemical properties of Feno-MPs are presented in Table 3. The particle size for all the Feno-MPs was about 4 µm. PLGA$_{54k}$ Feno-MPs exhibited a high drug loading of 16% with encapsulation efficacy of 96%. PLGA (50:50)$_{45k}$-PEG$_{5k}$ and PLGA/PLGA-PEG blends achieved drug loading of 25% and 18%, respectively. The morphology of Feno-MPs is shown in FIG. 10A.

TABLE 3

Physiochemical characterization of Feno-MPs

| Polymer | Particle size (μm) | DL (wt. %) | EE (%) |
|---|---|---|---|
| PLGA (50:50) $_{54k}$ | 3.8 ± 1.8 | 16 | 96 |
| PLGA (50:50)$_{45k}$-PEG$_{5k}$ | 4.0 ± 2.6 | 25 | 100 |
| PLGA (50:50)$_{45k}$-PEG$_{5k}$ : PLGA (50:50) $_{54k}$ (1:1 blend) | 4.0 ± 2.0 | 18 | 100 |

In vitro drug release profile of Feno-MPs. A significantly prolonged drug release (at least 4 months) was observed (FIG. 10B) for Feno-MPs. The blending of PLGA and PLGA-PEG generated a more linear and slower drug release in vitro than PLGA Feno-MPs or PLGA-PEG Feno-MPs alone (FIG. 10B). By further modifying the parameters including the particle size, molecular weight, and polymer type (PLA or PLGA with different LA:GA ratio), we could achieve even more prolonged drug release.

Figure 11:
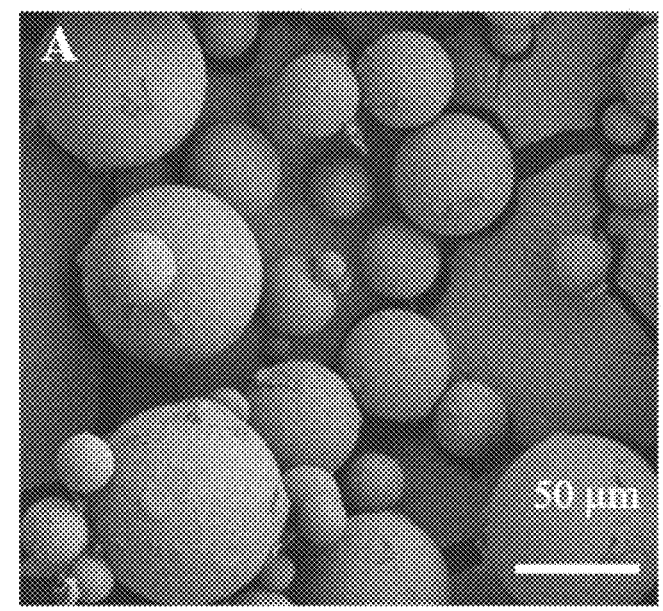
FIG. 11 shows in (A) a representative SEM image of Pemafibrate-loaded PLA$_{54k}$ microparticles (Pema-MP) with average particle size of 22.5±7.9 μm, and in (B) an in vitro drug release profile of PLA$_{54k}$ Pema-MP and PLA$_{76k}$ Pema-MP under sink conditions. Data are presented as average±SEM, n=3 repeats.
Figure 11:
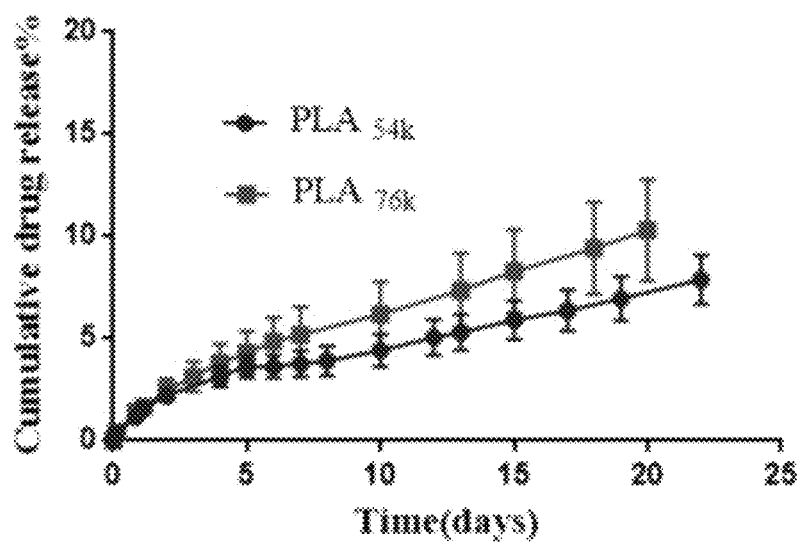

Physiochemical characterization of Pema-MPs. Physicochemical characteristics of Pema-MPs are shown in Table 4. Both types of the Pema-MPs have more than 15% drug loading and more than 75% encapsulation efficiency. The particle size of PLA$_{54k}$ and PLA$_{76k}$ Pema-MPs was around 22.5 μm and 24.6 μm, respectively. The morphology of Pema-MPs is shown in FIG. 11.

TABLE 4

Physicochemical characteristics of Pema-MP

| Polymer | Particle size (μm) | DL (wt. %) | EE (%) |
|---|---|---|---|
| PLA$_{54k}$ | 22.5 ± 7.9 | 15 | 75 |
| PLA$_{76k}$ | 24.6 ± 8.4 | 16 | 80 |

In vitro drug release profile of Pema-MPs. The in vitro drug release profile of Pema-MPs is shown in FIG. 11. No burst release was shown for both types of Pema-MPs. Both types of the Pema-MPs displayed less than 10% drug release in the first 20 days. The drug release studies are still on-going, and the two Pema-MPs have shown the ability to provide prolonged drug release. The drug release profile can be extended by adjusting the formulation parameters including the polymer concentration, homogenization speed, and emulsifier applied. The microparticle sizes are less than 25 μm, which can be injected through fine gauged needle (e.g. 30G), facilitating the pre-clinical and clinical use.

In certain non-limiting embodiments, the present disclosure is directed to a pharmaceutical nanoparticle and/or a microparticle, comprising an inner portion containing an agonist of peroxisome proliferator-activated receptor α (PPARα), disposed in a biodegradable polymer; and an outer coating comprising an emulsifier which surrounds the inner portion; and wherein at least about 5 wt % to about 25 wt % of the pharmaceutical particle comprises the agonist, and wherein the pharmaceutical particles have a sustained delayed release of the agonist in a range of at least about 1 to 12 months when in an aqueous solution or physiological environment. The agonist may be a fibrate and may be selected from the group consisting of fenofibrate, pemafibrate, clofibrate, gemfibrozil, ciprofibrate, bezafibrate, ABT-335, etofibrate, pirifibrate, and beclofibrate, and combinations thereof. The agonist may be selected from GW 9578, GW 7647, GW 590735, and GFT505. The biodegradable polymer may be selected from the group consisting of poly(hydroxy acids), poly(lactic acid), poly(glycolic acid), and poly(lactic acid-co-glycolic acid), poly(lactide), poly (glycolide), poly(lactide-co-glycolide), poly(lactide-co-caprolactone), polyanhydrides, polyorthoesters, polyamides, polycarbonates, polyalkylenes, polyethylene, polypropylene, polyalkylene glycols, poly(ethylene glycol), polyalkylene oxides, poly(ethylene oxide), polyalkylene terephthalates, poly(ethylene terephthalate), polyvinyl alcohols, polyvinyl ethers, polyvinyl esters, polyvinyl halides, poly (vinyl chloride), polyvinylpyrrolidone, polysiloxanes, poly (vinyl alcohols), poly(vinyl acetate), polystyrene, polyurethanes, poly(butyric acid), poly(valeric acid), celluloses, polyacrylates and polyacrylate derivatives, and co-polymers thereof. The biodegradable polymer may be a cellulose selected from the group consisting of alkyl celluloses, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxyethyl cellulose, cellulose triacetate, and cellulose sulphate sodium salt, and copolymers thereof. The biodegradable polymer may be a polyacrylate or polyacrylate derivative selected from the group consisting of polymers of acrylic acid, methacrylic acid, and methacrylate esters, poly (methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), and copolymers and blends thereof. The emulsifier may be selected from poly (vinyl alcohol) (PVA), polyethylene oxide-polypropylene oxide-polyethylene oxide polymers (PEO-PPO-PEO), polyoxyethylene sorbitan, surfactants, sucrose esters, and cholic acids. The biodegradable polymer may comprise poly (lactic acid-co-glycolic acid) (PLGA), and the emulsifier may comprise poly (vinyl alcohol) (PVA). In certain non-limiting embodiments, the present disclosure is directed to a method of treating in a subject a disorder or condition related to reduced peroxisome proliferator-activated receptor α (PPARα) activity, comprising administering to the subject in need of such therapy, a therapeutic amount of a pharmaceutical particle as described hereinabove. The disorder or condition may be an ocular disorder or condition selected from the group consisting of retinal inflammation, retinal neovascularization, retinal vascular leakage, retinopathy of prematurity (ROP), diabetic retinopathy (DR), an age-related macular degeneration (AMD), diabetic macular edema (DME), keratitis, endophthalmitis, blepharitis, conjunctivitis, scleritis, herpetic inflammation, uveitis, vasculitis, arteritis, orbital inflammations, optic neuritis, sympathetic ophthalmia, retinitis, macular edema, glaucoma, proliferative vitreoretinopathy, corneal edema, uveal edema, retinal edema, retinal artery or vein occlusion, corneal graft rejection, corneal neovascularization, neovascular glaucoma, and sickle cell retinopathy. In certain non-limiting embodiments, the present disclosure is directed to a kit, comprising the pharmaceutical particle described above, and instructions, including adverse indications, for use of the pharmaceutical particle in a treatment of a disorder or condition, as described elsewhere herein, in a subject. In certain embodiments, the disorder or condition is an ocular disorder or condition selected from the group consisting of retinal inflammation, retinal neovascularization, retinal vascular leakage, retinopathy of prematurity (ROP), diabetic retinopathy (DR), an age-related macular degeneration (AMD), diabetic macular edema (DME), keratitis, endophthalmitis, blepharitis, conjunctivitis, scleritis, herpetic inflammation, uveitis, vasculitis, arteritis, orbital inflammations, optic neuritis, sympathetic ophthalmia, retinitis, macular edema, glaucoma, proliferative vitreoretinopathy, corneal edema, uveal edema, retinal edema, retinal artery or vein occlusion, corneal graft rejection, corneal neovascularization, neovascular glaucoma, and sickle cell retinopathy.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in exemplary claims herein below, it is not intended that the present disclosure be limited to these particular exemplary claims.

What is claimed is:

1. A pharmaceutical particle, comprising: an inner portion comprising an agonist of peroxisome proliferator-activated receptor α (PPARα), disposed in a biodegradable polymer; and an outer coating comprising an emulsifier which surrounds the inner portion, wherein the biodegradable polymer comprises poly (lactic acid-co-glycolic acid) (PLGA), and the emulsifier is poly (vinyl alcohol) (PVA); and wherein at least about 5 wt % to about 25 wt % of the pharmaceutical particle comprises the agonist, and wherein the pharmaceutical particles have a sustained delayed release of the agonist in a range of at least about 1 to 12 months when in an aqueous solution or physiological environment.

2. The pharmaceutical particle of claim 1, wherein the particle has an average diameter in a range from about 100 nm to about 100 μm.

3. The pharmaceutical particle of claim 1, wherein the pharmaceutical particle is a nanosphere or microsphere.

4. The pharmaceutical particle of claim 1, wherein the agonist is a fibrate is selected from the group consisting of fenofibrate, pemafibrate, clofibrate, gemfibrozil, ciprofibrate, bezafibrate, ABT-335, etofibrate, pirifibrate, and beclofibrate, and combinations thereof.

5. The pharmaceutical particle of claim 1, wherein the agonist is selected from GW 9578, GW 7647, GW 590735, and GFT505.

6. The pharmaceutical particle of claim 1, further comprising poly(ethylene glycol).

7. A pharmaceutical particle, comprising: an inner portion comprising an agonist of peroxisome proliferator-activated receptor α (PPARα), disposed in a biodegradable polymer; and an outer coating comprising an emulsifier which surrounds the inner portion, wherein the biodegradable polymer comprises poly (lactic acid) (PLA), and the emulsifier is poly (vinyl alcohol) (PVA); and wherein at least about 5 wt % to about 25 wt % of the pharmaceutical particle comprises the agonist, and wherein the pharmaceutical particles have a sustained delayed release of the agonist in a range of at least about 1 to 12 months when in an aqueous solution or physiological environment.

8. The pharmaceutical particle of claim 7, wherein the particle has an average diameter in a range from about 100 nm to about 100 μm.

9. The pharmaceutical particle of claim 7, wherein the pharmaceutical particle is a nanosphere or microsphere.

10. The pharmaceutical particle of claim 7, wherein the agonist is a fibrate is selected from the group consisting of fenofibrate, pemafibrate, clofibrate, gemfibrozil, ciprofibrate, bezafibrate, ABT-335, etofibrate, pirifibrate, and beclofibrate, and combinations thereof.

11. The pharmaceutical particle of claim 7, wherein the agonist is selected from GW 9578, GW 7647, GW 590735, and GFT505.

12. The pharmaceutical particle of claim 7, further comprising poly(ethylene glycol).

* * * * *